United States Patent
Kurata et al.

(10) Patent No.: US 10,755,181 B2
(45) Date of Patent: Aug. 25, 2020

(54) INFORMATION PROCESSING APPARATUS, INFORMATION PROCESSING METHOD, AND INFORMATION PROCESSING SYSTEM FOR STATUS RECOGNITION

(71) Applicant: SONY CORPORATION, Tokyo (JP)

(72) Inventors: Masatomo Kurata, Tokyo (JP); Masanori Katsu, Tokyo (JP); Sota Matsuzawa, Tokyo (JP)

(73) Assignee: SONY CORPORATION, Tokyo (JP)

(*) Notice: Subject to any disclaimer, the term of this patent is extended or adjusted under 35 U.S.C. 154(b) by 752 days.

(21) Appl. No.: 15/103,984

(22) PCT Filed: Sep. 22, 2014

(86) PCT No.: PCT/JP2014/075117
§ 371 (c)(1),
(2) Date: Jun. 13, 2016

(87) PCT Pub. No.: WO2015/098215
PCT Pub. Date: Jul. 2, 2015

(65) Prior Publication Data
US 2016/0314401 A1 Oct. 27, 2016

(30) Foreign Application Priority Data
Dec. 24, 2013 (JP) ................. 2013-265274

(51) Int. Cl.
*G06N 5/04* (2006.01)
*G06F 3/01* (2006.01)
(Continued)

(52) U.S. Cl.
CPC .................. *G06N 5/04* (2013.01); *A61B 5/11* (2013.01); *G06F 1/163* (2013.01); *G06F 3/01* (2013.01);
(Continued)

(58) Field of Classification Search
CPC . G06N 5/04; G06F 1/163; G06F 3/011; G06F 11/30; G06F 3/01; H04M 1/72522;
(Continued)

(56) References Cited

U.S. PATENT DOCUMENTS

| | | | |
|---|---|---|---|
| 2011/0313956 A1* | 12/2011 | Abe | G06F 17/30241 706/12 |
| 2013/0072765 A1 | 3/2013 | Kahn et al. | |
| 2013/0106603 A1* | 5/2013 | Weast | A61B 5/11 340/539.11 |

FOREIGN PATENT DOCUMENTS

| | | |
|---|---|---|
| JP | 2010-081419 A | 4/2010 |
| JP | 2010-176307 A | 8/2010 |
| JP | 2010-178982 A | 8/2010 |

OTHER PUBLICATIONS

Extended European Search Report of EP Patent Application No. 14874356.0, dated Aug. 3, 2017, 9 pages.

(Continued)

*Primary Examiner* — Shane D Woolwine
(74) *Attorney, Agent, or Firm* — Chip Law Group

(57) ABSTRACT

Provided is an information processing apparatus including a status recognition unit that recognizes a status of a reference apparatus on the basis of information on a status of an apparatus corresponding to the reference apparatus, the reference apparatus serving as a reference when a behavior recognition mode for deciding a status of behavior is set and a behavior-recognition-mode setting unit that sets the behavior recognition mode for a setting target apparatus for which the behavior recognition mode is to be set on the basis of the recognized status of the reference apparatus.

16 Claims, 17 Drawing Sheets

(51) Int. Cl.
    *G06F 11/30*     (2006.01)
    *A61B 5/11*     (2006.01)
    *H04M 1/725*     (2006.01)
    *G06F 1/16*     (2006.01)
    *A61B 5/00*     (2006.01)

(52) U.S. Cl.
    CPC .............. *G06F 3/011* (2013.01); *G06F 11/30* (2013.01); *H04M 1/7253* (2013.01); *H04M 1/72569* (2013.01); *A61B 5/68* (2013.01); *A61B 2560/0223* (2013.01); *H04M 1/72522* (2013.01); *H04M 1/72563* (2013.01); *H04M 2250/06* (2013.01); *H04M 2250/10* (2013.01)

(58) Field of Classification Search
    CPC ......... H04M 1/72563; H04M 1/72569; H04M 1/72523; H04M 2250/06; H04M 2250/10; A61L 35/11; A61L 35/68
    USPC ......................................................... 706/11
    See application file for complete search history.

(56) References Cited

OTHER PUBLICATIONS

International Search report on patentability received for PCT Application No. PCT/JP2014/075117, dated Dec. 22, 2014, pp. 1.

Office Action for CN Patent Application No. 201480068697.4, dated Dec. 27, 2018, 12 pages of Office Action and 19 pages of English Translation.

Office Action for JP Patent Application No. 2015-554609, dated Oct. 16, 2018, 5 pages of Office Action and 3 pages of English Translation.

\* cited by examiner

FIG. 3

|  | FIRST INFORMATION PROCESSING APPARATUS 100 | | SECOND INFORMATION PROCESSING APPARATUS 200A | SECOND INFORMATION PROCESSING APPARATUS 200B |
|---|---|---|---|---|
|  | SMARTPHONE | | WRISTBAND | ANKLE-WORN APPARATUS |
| SENSOR | ACCELERATION | | ACCELERATION | ACCELERATION |
|  | GPS | | — | — |
| RELATIVE DISTANCE |  | | SHORT | SHORT |
| RECOGNITION RESULT: FIRST INFORMATION PROCESSING APPARATUS 100 | DURING STAY | SITTING |  |  |
|  |  | STANDING |  |  |
|  | DURING TRANSFER | BICYCLE |  |  |
|  |  | TRAIN |  |  |
|  |  | CAR |  |  |
| BEHAVIOR-RECOGNITION-MODE TO BE SELECTED: SECOND INFORMATION PROCESSING APPARATUS 200 |  |  | RECOGNITION OF WHETHER USER IS EATING MEAL | RECOGNITION OF JIGGLING OF USER'S KNEE |
|  |  |  |  | CADENCE DETECTION |
|  |  |  | DOZE (SLEEP) DETECTION |  |
|  |  |  | DRIVING RECOGNITION (STEERING WHEEL) | DRIVING RECOGNITION (ACCELERATOR) |

| | FIRST INFORMATION PROCESSING APPARATUS 100 | | SECOND INFORMATION PROCESSING APPARATUS 200A | | SECOND INFORMATION PROCESSING APPARATUS 200B |
|---|---|---|---|---|---|
| | APPARATUS ATTACHED TO WAIST (CLIP) | | HMD | | APPARATUS HUNG AROUND NECK |
| SENSOR | ACCELERATION, GYRO, GEOMAGNETIC | | ACCELERATION, GYRO | | ACCELERATION, IR SENSOR |
| | | | GPS | | |
| RECOGNITION RESULT: FIRST INFORMATION PROCESSING APPARATUS 100 | DURING STAY | STANDING | RECOGNITION OF NOD | | RECOGNITION OF HUG |
| | | LYING | RECOGNITION OF SLEEP LEVEL | | RECOGNITION OF SLEEP LEVEL, RECOGNITION OF BREATH |
| | DURING TRANSFER | WALKING | PEDESTRIAN DEAD RECKONING (PDR) | | |
| BEHAVIOR-RECOGNITION MODE TO BE SELECTED: SECOND INFORMATION PROCESSING APPARATUS 200 | | TEMPORARI STOPPING | MEASUREMENT BY GPS | | RECOGNITION OF WHO IS PRESENT BY IR SENSOR |

FIG. 5

| | FIRST INFORMATION PROCESSING APPARATUS 100 | | SECOND INFORMATION PROCESSING APPARATUS 200A | SECOND INFORMATION PROCESSING APPARATUS 200B |
|---|---|---|---|---|
| | APPARATUS ATTACHED TO WAIST (CLIP) | | EYEWEAR | WRISTBAND |
| SENSOR | ACCELERATION, GYRO, GEOMAGNETIC | | ACCELERATION, GYRO, GEOMAGNETIC | ACCELERATION, GYRO |
| | GPS | | | |
| RECOGNITION RESULT: FIRST INFORMATION PROCESSING APPARATUS 100 | APPARATUS IS LEFT | POOL (POI) | | |
| | DURING TRANSFER | STOPPING, WALKING & GOLF COURSE (POI) | | |
| | DURING TRANSFER | CAR | | |
| BEHAVIOR-RECOGNITION-MODE TO BE SELECTED: SECOND INFORMATION PROCESSING APPARATUS 200 | | | RECOGNITION OF SWIMMING STYLE, RECOGNITION OF BREATH & TURN | RECOGNITION OF SWIMMING STYLE |
| | | | RECOGNITION OF SWING (ATTITUDE OF HEAD) | RECOGNITION OF SWING (ATTITUDE OF ARM) |
| | | | EYE GAZE RECOGNITION (FACE DIRECTION) | DRIVING RECOGNITION (STEERING) |

FIG. 6

| | FIRST INFORMATION PROCESSING APPARATUS 100 | SECOND INFORMATION PROCESSING APPARATUS 200A | SECOND INFORMATION PROCESSING APPARATUS 200B | SECOND INFORMATION PROCESSING APPARATUS 200C |
|---|---|---|---|---|
| | SMARTPHONE | RING | NECKLACE | EYEWEAR |
| SENSOR | ACCELERATION | ACCELERATION | ACCELERATION | ACCELERATION |
| | GPS | VITAL | | CAMERA |
| RECOGNITION RESULT: FIRST INFORMATION PROCESSING APPARATUS 100 / BEHAVIOR-RECOGNITION MODE TO BE SELECTED: SECOND INFORMATION PROCESSING APPARATUS 200 | SITTING IN RESTAURANT | RECOGNITION OF CONTENT OF MEAL (BLOOD-SUGAR MONITORING) | | RECOGNITION OF CONTENT OF MEAL (IMAGE) |
| | SITTING IN OFFICE | DESK WORK RECOGNITION (TYPING/WRITING/READING/ETC.) | | CAMERA IS TURNED OFF |
| | APPARATUS IS LEFT NEAR OCEAN + DISTANCE IS LONG | RECOGNITION OF WHETHER USER IS ALIVE | BREATH RECOGNITION | SURFING RECOGNITION FOR CREATING DIGEST |

FIG. 9
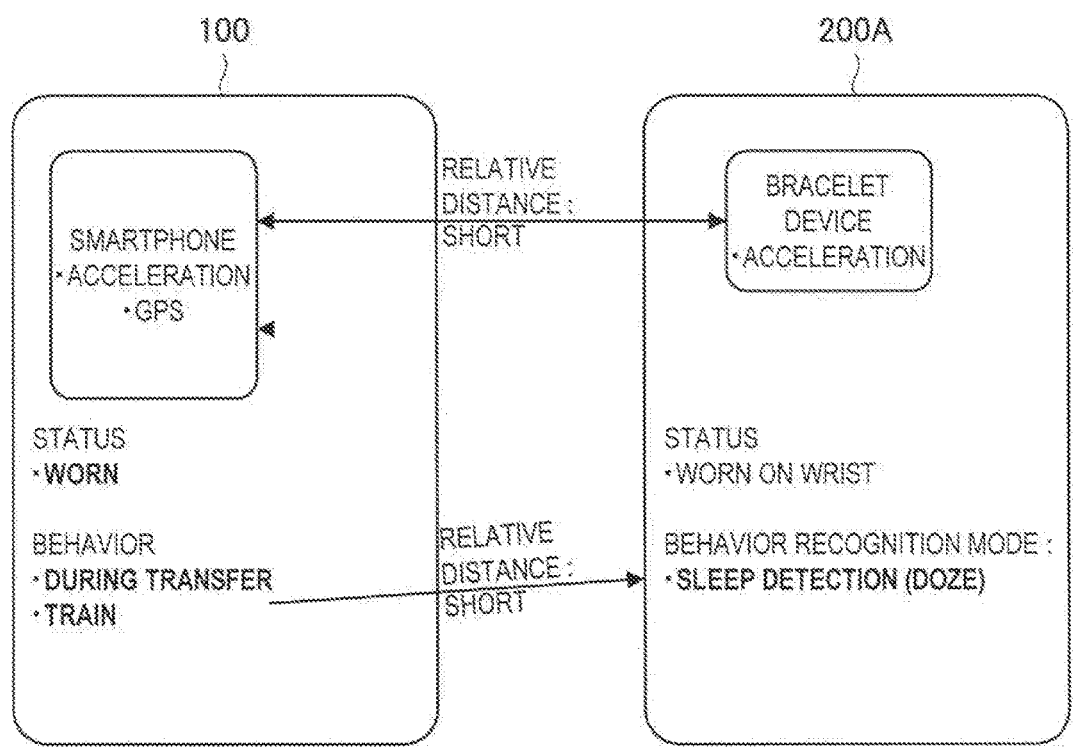
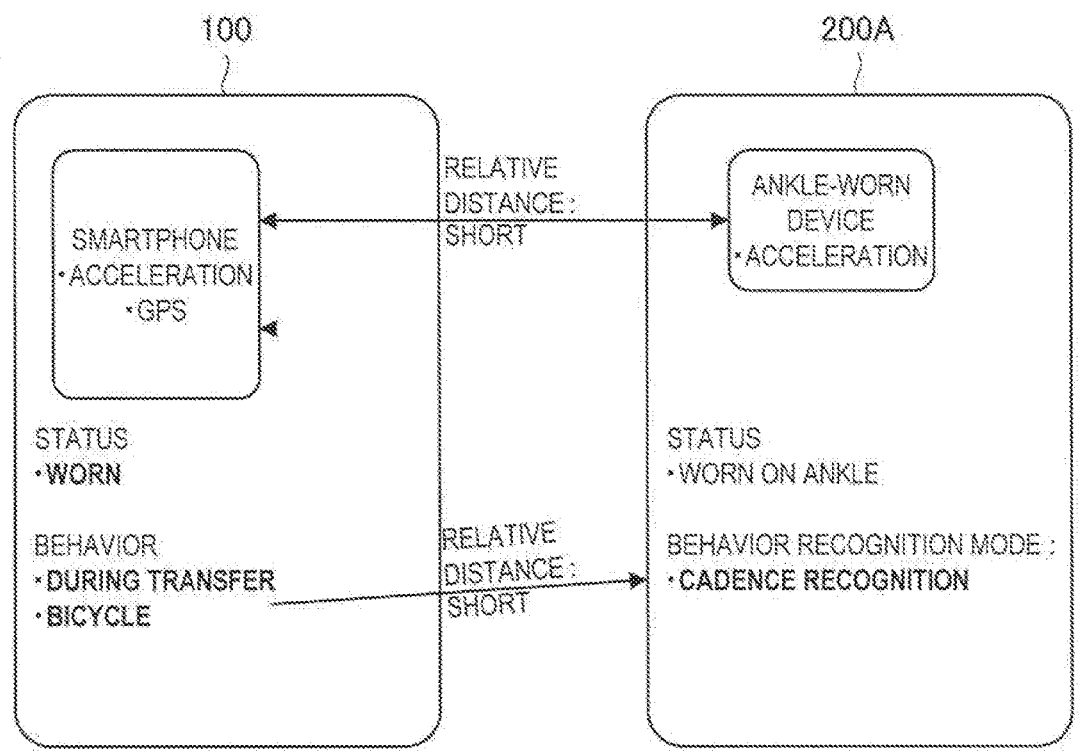

INFORMATION PROCESSING APPARATUS, INFORMATION PROCESSING METHOD, AND INFORMATION PROCESSING SYSTEM FOR STATUS RECOGNITION

CROSS REFERENCE TO RELATED APPLICATIONS

This application is a U.S. National Phase of International Patent Application No. PCT/JP2014/075117 filed on Sep. 22, 2014, which claims priority benefit of Japanese Patent Application No. JP 2013-265274 filed in the Japan Patent Office on Dec. 24, 2013. Each of the above-referenced applications is hereby incorporated herein by reference in its entirety.

TECHNICAL FIELD

The present disclosure relates to information processing apparatuses, information processing methods, programs, and information processing systems.

BACKGROUND ART

Technologies for recognizing behavior of a user and displaying a result of the recognition on a display screen have been developed. Examples of the technologies for recognizing behavior of a user and displaying a result of the recognition on a display screen include a technology described in the following Patent Literature 1.

CITATION LIST

Patent Literature

Patent Literature 1: JP 2010-134802A

SUMMARY OF INVENTION

Technical Problem

In recent years, the number of users who use wearable-type apparatuses (hereinafter, referred to as "wearable apparatuses") that the users can use while wearing it, such as not only portable apparatuses like smartphones but also wrist-watch-type devices, has been increasing. In addition, such as Lifelog, applications relating to behavior of a user also have been put to practical use, the applications using detection values from sensors loaded into the above-described apparatuses or external sensors attached to the above-described apparatuses.

However, in the case where behavior of a user is recognized using the detection values from the sensor, for example, there is a possibility that the behavior of the user is not recognized due to a status of the apparatus loaded with the sensor (or the apparatus to which the external sensor is attached), for example.

The present disclosure proposes a novel and improved information processing apparatus, information processing method, program, and information processing system capable of recognizing behavior of a user with a higher accuracy.

Solution to Problem

According to the present disclosure, there is provided an information processing apparatus including: a status recognition unit configured to recognize a status of a reference apparatus on the basis of information on a status of an apparatus corresponding to the reference apparatus, the reference apparatus serving as a reference when a behavior recognition mode for deciding a status of behavior is set; and a behavior-recognition-mode setting unit configured to set the behavior recognition mode for a setting target apparatus for which the behavior recognition mode is to be set on the basis of the recognized status of the reference apparatus.

According to the present disclosure, there is provided an information processing apparatus including: a setting unit configured to configure a setting relating to behavior recognition on the basis of information indicating a behavior recognition mode for deciding a status of acquired behavior; and a processing unit configured to carry out a process relating to the behavior recognition according to the configured setting relating to the behavior recognition.

According to the present disclosure, there is provided an information processing method carried out by an information processing apparatus, the method including: a step of recognizing a status of a reference apparatus on the basis of information on a status of an apparatus corresponding to the reference apparatus, the reference apparatus serving as a reference of a behavior recognition mode for deciding a status of behavior; and a step of setting the behavior recognition mode for a setting target apparatus for which the behavior recognition mode is to be set on the basis of the recognized status of the reference apparatus.

According to the present disclosure, there is provided a program causing a computer to execute: a step of recognizing a status of a reference apparatus on the basis of information on a status of an apparatus corresponding to the reference apparatus, the reference apparatus serving as a reference of a behavior recognition mode for deciding a status of behavior; and a step of setting the behavior recognition mode for a setting target apparatus for which the behavior recognition mode is to be set on the basis of the recognized status of the reference apparatus.

According to the present disclosure, there is provided an information processing system including: a first information processing apparatus configured to set a behavior recognition mode for a setting target apparatus for which the behavior recognition mode for deciding a status of behavior is to be set; and one or more of second information processing apparatuses each of which is the setting target apparatus and each of which is configured to carry out a process relating to behavior recognition on the basis of the set behavior recognition mode. The first information processing apparatus includes a status recognition unit configured to recognize a status of a reference apparatus on the basis of information on a status of an apparatus corresponding to the reference apparatus, the reference apparatus serving as a reference of the behavior recognition mode, and a behavior-recognition-mode setting unit configured to set the behavior recognition mode for each of the second information processing apparatuses on the basis of the recognized status of the reference apparatus.

Advantageous Effects of Invention

According to the present disclosure, it is possible to recognize behavior of a user with a higher accuracy.

Note that the effects described above are not necessarily limited, and along with or instead of the effects, any effect

BRIEF DESCRIPTION OF DRAWINGS

FIG. 3 is an explanatory diagram illustrating an example of a process in an information processing method according to the present embodiment.

FIG. 4 is an explanatory diagram illustrating an example of a process in an information processing method according to the present embodiment.

FIG. 5 is an explanatory diagram illustrating an example of a process in an information processing method according to the present embodiment.

FIG. 6 is an explanatory diagram illustrating an example of a process in an information processing method according to the present embodiment.

FIG. 9 is an explanatory diagram illustrating a third example of a behavior-recognition-mode setting process in an information processing method according to the present embodiment.

DESCRIPTION OF EMBODIMENT(S)

Figure 1:
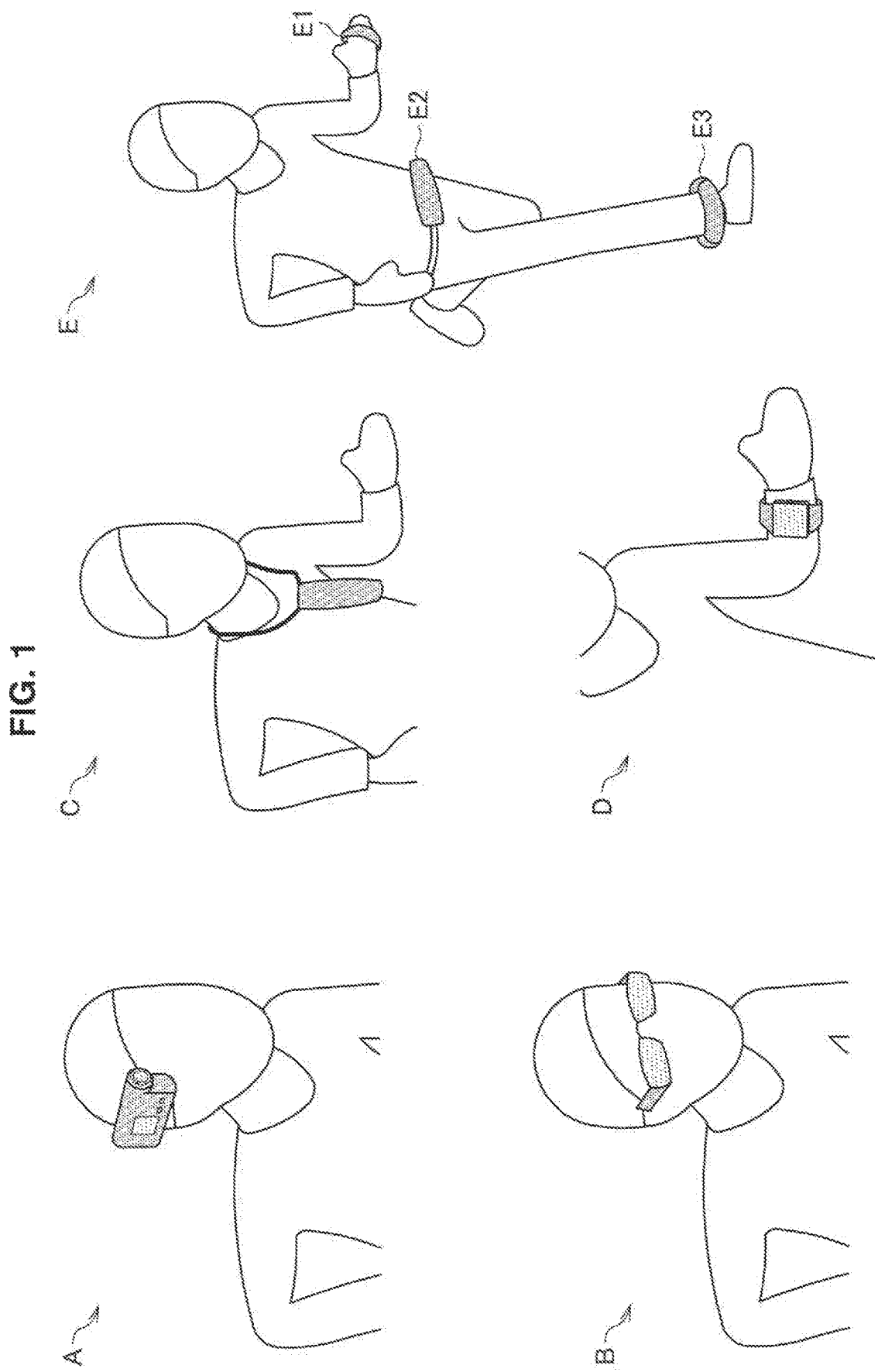
FIG. 1 is an explanatory diagram illustrating an example of wearable apparatuses according to the present embodiment.

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

Note that the description is given in the following order.
1. Information Processing Method according to Present Embodiment
2. Information Processing System according to First Embodiment
3. Information Processing System according to Second Embodiment
4. Program according to Present Embodiment

Information Processing Method According to Present Embodiment

First, an information processing method according to the present embodiment will be described before description of configurations of respective apparatuses constituting an information processing system according to the present embodiment. Hereinafter, an apparatus for carrying out a process in the information processing method according to the present embodiment is referred to as a "first information processing apparatus" among the apparatuses constituting the information processing system according to the present embodiment.

As described above, in the case where behavior of a user is recognized using the detection values from the sensor, for example, there is a possibility that the behavior of the user is not recognized due to a status of the apparatus loaded with the sensor (or the apparatus to which the external sensor is attached).

Therefore, the first information processing apparatus according to the present embodiment sets, for example, a behavior recognition mode for a setting target apparatus on the basis of a status and the like of a reference apparatus.

Here, the reference apparatus according to the present embodiment is an apparatus serving as a reference when the behavior recognition mode is to be set. Examples of the reference apparatus according to the present embodiment include an apparatus loaded with a sensor relating to recognition of behavior of a user, and an apparatus to which an external sensor relating to recognition of behavior of a user is attached. Specifically, the examples of the reference apparatus according to the present embodiment include a wearable apparatus and portable apparatuses such as a smartphone, a mobile phone, and a tablet apparatus.

In the information processing system according to the present embodiment, the first information processing apparatus according to the present embodiment serves as the reference apparatus according to the present embodiment, for example. Note that, the reference apparatus according to the present embodiment is not limited to the first information processing apparatus according to the present embodiment.

For example, the reference apparatus according to the present embodiment may be an apparatus other than the first information processing apparatus according to the present embodiment. For example, in the case where the reference apparatus according to the present embodiment is not deemed to be the setting target apparatus according to the present embodiment, the reference apparatus according to the present embodiment may be an apparatus that does not constitute the information processing system according to the present disclosure.

The setting target apparatus according to the present embodiment is a target apparatus for which the behavior recognition mode is to be set. Examples of the setting target apparatus according to the present embodiment include one or more apparatuses other than the reference apparatus. The setting target apparatus according to the present embodiment may be the reference apparatus only, or may be the reference device and one or more apparatuses other than the reference device, for example. Hereinafter, a setting target apparatus other than the reference apparatus is referred to as a "second information processing apparatus" among the setting target apparatuses according to the present embodiment. In other words, the second information processing apparatus according to the present embodiment is the setting target apparatus and is not the reference apparatus.

Examples of the setting target apparatus according to the present embodiment include an apparatus loaded with a sensor relating to recognition of behavior of a user, and an apparatus to which an external sensor relating to recognition of behavior of a user is attached. Specifically, the examples of the setting target apparatus according to the present embodiment include a wearable apparatus and portable apparatuses such as a smartphone, a mobile phone, and a tablet apparatus.

FIG. 1 is an explanatory diagram illustrating an example of wearable apparatuses according to the present embodiment. Examples A to E in FIG. 1 each illustrates an example of the wearable apparatus.

As illustrated in FIG. 1, examples of the wearable apparatus according to the present embodiment include the following apparatuses, the wearable apparatus being capable of serving as the reference apparatus according to the present embodiment or the setting target apparatus according to the present embodiment. Of course, the wearable apparatus according to the present embodiment is not limited to the following examples.

Head-mounted apparatus (example A in FIG. 1): for example, a head-mounted display (HMD) or imaging apparatus.

Eyewear apparatus (example B in FIG. 1): for example, an HMD or glasses apparatus.

Apparatus hung around neck (example C in FIG. 1): for example, an imaging apparatus, headset, necklace apparatus, or data logger.

Wrist/arm-worn apparatus (example D in FIG. 1): for example, a wristwatch apparatus, data logger, bracelet apparatus, or wristband apparatus.

Hand/finger-worn apparatus (example E1 in FIG. 1): for example, a glove apparatus, or ring apparatus.

Apparatus attached to waist/jacket/pocket (example E2 in FIG. 1): for example, a belt apparatus, clip/refrigerator magnet type apparatus, or data logger.

Ankle/leg-worn apparatus (example E3 in FIG. 1): for example, an anklet apparatus, or data logger.

Examples of the sensor relating to recognition of behavior of a user according to the present embodiment include an acceleration sensor, Global Positioning System (GPS) device, gyro sensor, atmospheric pressure sensor, proximity sensor, biosensor, etc. Note that, the sensor relating to recognition of behavior of a user according to the present embodiment is not limited thereto. The sensor may be any sensor usable for a process for behavior recognition of the user.

The behavior recognition mode according to the present embodiment is a mode for deciding a status of behavior. The behavior recognition mode indicates a single setting relating to the behavior recognition, or a combination of a plurality of settings relating to the behavior recognition.

Examples of the behavior recognition mode according to the present embodiment include one or a combination of two or more of "types of sensors to be used for behavior recognition, or parameters of the sensors", "types of feature amounts used for behavior recognition among detection values from the sensors", an "algorithm or model data used for a process for behavior recognition", and the like. Here, the "types of sensors to be used for behavior recognition, or parameters of the sensors" correspond to settings relating to the sensors. In addition, the "types of feature amounts used for behavior recognition among detection values from the sensors" and the "algorithm or model data used for a process for behavior recognition" correspond to settings relating to the process for behavior recognition, for example.

For example, setting of the behavior recognition mode configured by the first information processing apparatus according to the present embodiment means that the first information processing apparatus according to the present embodiment transmits information indicating the behavior recognition mode to a setting target apparatus and causes the setting target apparatus to configure settings relating to behavior recognition. The first information processing apparatus according to the present embodiment causes, for example, a communication unit (to be described later) included in the first information processing apparatus according to the present embodiment or an external communication device connected to the first information processing apparatus according to the present embodiment to transmit information indicating the behavior recognition mode to the setting target apparatus so as to cause the setting target apparatus to configure settings relating to behavior recognition.

Note that, it is also possible for the first information processing apparatus according to the present embodiment to set its own apparatus (first information processing apparatus according to the present embodiment) as the setting target apparatus and set the behavior recognition mode of the own apparatus. In the case where the own apparatus is the setting target apparatus, setting of the behavior recognition mode configured by the first information processing apparatus according to the present embodiment means that "the first information processing apparatus according to the present embodiment configures settings relating to behavior recognition on the basis of information indicating the behavior recognition mode", for example.

The information indicating the behavior recognition mode according to the present embodiment includes one or both of data indicating settings relating to the sensors and data indicating settings relating to the process for behavior recognition, for example. The information indicating the behavior recognition mode according to the present embodiment may include an order to configure settings relating to behavior recognition, for example.

Examples of the data indicating settings relating to the sensors according to the present embodiment include one or both of the following data. Note that, the data indicating settings relating to the sensors according to the present embodiment is not limited to the following examples. Examples of the data indicating settings relating to the sensors according to the present embodiment include any data (or data group) capable of controlling operation of the sensors.

Data indicating types of sensors to be activated (for example, sensor ID)

Data indicating parameters of the sensor

Examples of the data indicating settings relating to the process for behavior recognition according to the present embodiment include one or more of the following data. Note that, the data indicating settings relating to the process for behavior recognition according to the present embodiment is not limited to the following examples. Examples of the data indicating settings relating to the process for behavior recognition according to the present embodiment include any data (or data group) capable of controlling the process for behavior recognition.

Data indicating types of feature amounts (for example, IDs indicating the feature amounts)

Data indicating an algorithm used for a process for behavior recognition (for example, program data, and ID indicating algorithm)

Data indicating model data used for a process for behavior recognition (for example, model data itself, and ID indicating the model data)

The first information processing apparatus according to the present embodiment sets the behavior recognition mode for the setting target apparatus. Thereby the process for behavior recognition is carried out in the setting target apparatus according to the setting relating to behavior recognition indicated by the set behavior recognition mode. Here, the first information processing apparatus according to the present embodiment sets the behavior recognition mode for the setting target apparatus on the basis of a status and the like of a reference apparatus. Therefore, it is possible to switch the behavior recognition mode to be set for the setting target apparatus. In other words, since the first information processing apparatus according to the present embodiment sets the behavior recognition mode for the setting target apparatus, it is possible to switch the process for behavior recognition to be carried out in the setting target apparatus.

Accordingly, since the first information processing apparatus according to the present embodiment carries out the process relating to the information processing method according to the present embodiment, it is possible to recognize behavior in a setting more suitable for the setting target apparatus. Therefore, it is possible to recognize behavior of a user with a higher accuracy.

Hereinafter, details of the process relating to the information processing method according to the present embodiment will be described using an example of the information processing system according to the present embodiment.

Information Processing System According to First Embodiment

First, a master-slave type information processing system will be described. In the master-slave type information processing system, the first information processing apparatus according to the present embodiment serves as an information processing system for setting a behavior recognition mode of a second information processing apparatus according to the present embodiment, in other words, the first information processing apparatus according to the present embodiment serves as a master, and the second information processing apparatus serves as a slave.

Hereinafter, the case where the first information processing apparatus according to the present embodiment is the reference apparatus is mainly used as an example. Note that, as described above, the reference apparatus according to the present embodiment may be an apparatus other than the first information processing apparatus according to the present embodiment.

Figure 2:
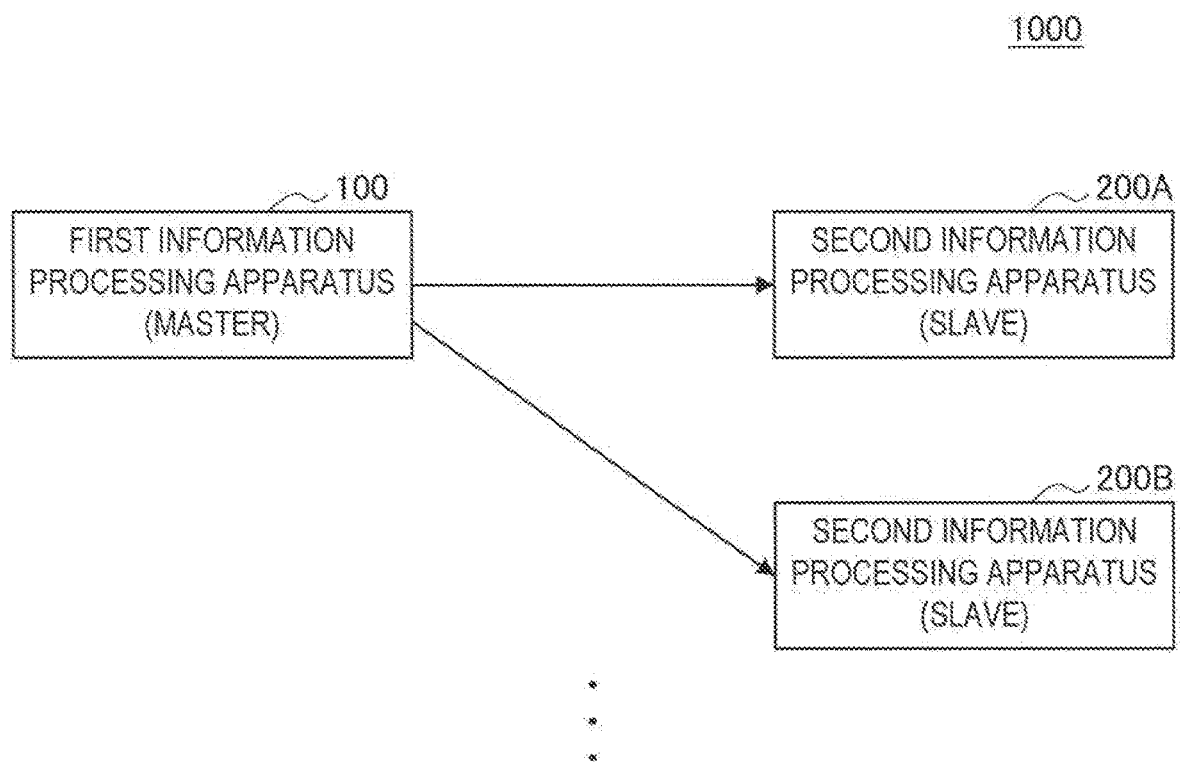
FIG. 2 is an explanatory diagram illustrating an example of an information processing system according to a first embodiment.

FIG. 2 is an explanatory diagram illustrating an example of an information processing system 1000 according to the first embodiment. The information processing system 1000 includes a first information processing apparatus 100, second information processing apparatuses 200A, 200B, . . . , for example. Hereinafter, a set of the second information processing apparatuses 200A, 200B, . . . , or one of the second information processing apparatuses 200A, 200B, . . . , may be referred to as a "second information processing apparatus 200".

FIG. 2 illustrates the example in which the information processing system according to the first embodiment includes a plurality of the second information processing apparatuses 200. However, the configuration of the information processing system according to the first embodiment is not limited thereto. For example, the information processing system according to the first embodiment may include only one second information processing apparatus 200.

[1] Process in First Information Processing Apparatus 100

In the information processing system 1000, the first information processing apparatus 100 sets a behavior recognition mode for a setting target apparatus on the basis of a status and the like of a reference apparatus.

Examples of the setting target apparatus for which the first information processing apparatus 100 sets the behavior recognition mode include the second information processing apparatus 200. In the case where the behavior recognition mode is to be set for the second information processing apparatus 200, the first information processing apparatus 100 transmits information indicating the behavior recognition mode to the second information processing apparatus 200 to set the behavior recognition mode for the second information processing apparatus 200. Note that, it is also possible for the first information processing apparatus 100 to set its own apparatus as the setting target apparatus and set the behavior recognition mode of the own apparatus.

More specifically, for example, the first information processing apparatus 100 sets the behavior recognition mode for the setting target apparatus by carrying out (1) a status recognition process and (2) a behavior-recognition-mode setting process.

(1) Status Recognition Process

The first information processing apparatus 100 recognizes a status of the reference apparatus on the basis of information on a status of an apparatus corresponding to the reference apparatus. For example, the first information processing apparatus 100 may always carry out the status recognition process, or may carry out the status recognition process periodically or non-periodically.

Examples of the status of the apparatus according to the present embodiment include a "status where the apparatus is left" and a "status where the apparatus is attached to a user" such as the case where the user is wearing the apparatus or the case where the user is carrying the apparatus. More specifically, Examples of the "status where the apparatus is attached to a user" include a status where the apparatus is worn on a wrist, a status where the apparatus is attached to a jacket using a clip, a status where the apparatus is in a pants pocket, a status where the apparatus is in a backpack, and a status where the apparatus is held by a hand.

The information on the status of the apparatus according to the present embodiment is data for detecting such a status of the apparatus. More specifically, examples of the information on the status of the apparatus according to the present embodiment include the following data (or data groups).

[Examples of Information on Status of Apparatus in "Status where Apparatus is Left"]
- Location information (for example, data indicating latitude/longitude, point of interest (POI), specific location such as home or office)
- Sensor data indicating an attitude of the apparatus
- Data relating to the apparatus such as information on whether a battery is being charged
- Data indicating a status of the apparatus designated on the basis of a user operation

[Examples of Information on Status of Apparatus in "Status where Apparatus is Attached to User"]
- Sensor data (for example, acceleration data, detection values, or electrical signal indicating status of attachment part)
- Data indicating whether a button is pressed (for example, electrical signal according to button operation, or flag indicating whether button is pressed)
- Data indicating a status of the apparatus designated on the basis of a user operation As described above, examples of the information on the status of the apparatus according to the present embodiment include the detection values from the sensors included in the apparatus corresponding to the status (or external sensors attached to the target apparatus) and/or data indicating the status of the apparatus based on the user operation. Note that, the information on the status of the apparatus according to the present embodiment is not limited to the above described examples. The information on the status of the apparatus according to the present embodiment may be any data (or data group) by which the first information processing apparatus 100 can recognize the status of the apparatus according to the present embodiment.

In the case where the status of the reference apparatus is to be recognized on the basis of a detection value from the sensor (example of information on the status of the apparatus), the first information processing apparatus 100 uses a detection value transmitted from a sensor included in the first information processing apparatus 100 or an external sensor connected to the first information processing apparatus 100, for example (when the first information processing apparatus 100 is the reference apparatus). On the other hand, in the case where the status of the reference apparatus is to be recognized on the basis of a detection value from the sensor (example of information on the status of the apparatus), it is also possible for the first information processing apparatus 100 to use a detection value from a sensor acquired from the external reference apparatus through communication via a network (or through direct communication) (when the first information processing apparatus 100 is not the reference apparatus). The first information processing apparatus 100 recognizes the status of the apparatus on the basis of the detection value from the sensor by using any technology for recognizing the status of the apparatus with use of detection values from one or more sensors, such as pattern matching or threshold processing.

In the case where the status of the reference apparatus is to be recognized on the basis of data indicating the status of the apparatus based on a user operation (example of information on the status of the apparatus), the first information processing apparatus 100 uses data indicating the status of the apparatus based on the user operation, the data being transmitted from an operation unit (to be described later) included in the first information processing apparatus 100 or an external operation device connected to the first information processing apparatus 100, for example (when the first information processing apparatus 100 is the reference apparatus). On the other hand, in the case where the status of the reference apparatus is to be recognized on the basis of data indicating the status of the apparatus based on a user operation (example of information on the status of the apparatus), it is also possible for the first information processing apparatus 100 to use data indicating the status of the apparatus based on the user operation, the data having been acquired from the external reference apparatus through communication via a network (or through direct communication) (when the first information processing apparatus 100 is not the reference apparatus). The first information processing apparatus 100 recognizes the status indicated by the data indicating the status of the apparatus based on the user operation as the status of the apparatus, for example.

(2) Behavior-Recognition-Mode Setting Process

The first information processing apparatus 100 sets a behavior recognition mode for the setting target apparatus on the basis of the status of the reference apparatus recognized in the above described process (1) (status recognition process).

The first information processing apparatus 100 carries out the behavior-recognition-mode setting process with each recognition of the status of the reference apparatus in the above described process (1) (status recognition process), for example. Alternatively, the first information processing apparatus 100 may carry out the behavior-recognition-mode setting process with each change in the status of the reference apparatus recognized in the above described process (1) (status recognition process), for example.

It is also possible for the first information processing apparatus 100 to set the behavior recognition mode further on the basis of behavior-recognition-result information corresponding to the reference apparatus.

In the case where the behavior recognition mode is set further on the basis of the behavior-recognition-result information, the first information processing apparatus 100 carries out the behavior-recognition-mode setting process with each recognition of the status of the reference apparatus in the above described process (1) (status recognition process) and/or with each acquisition of behavior-recognition-result information, for example. Alternatively, the first information processing apparatus 100 may carry out the behavior-recognition-mode setting process with each change in the status of the reference apparatus recognized in the above described process (1) (status recognition process) and/or with each change in a result of recognizing the behavior of the user indicated by the behavior-recognition-result information, for example.

The behavior-recognition-result information according to the present embodiment is data indicating a result of recognizing behavior of the user. Examples of the recognized behavior of the user indicated by the behavior-recognition-result information according to the present embodiment include the following behavior in (a) to (d). Of course, the recognized behavior of the user indicated by the behavior-recognition-result information according to the present embodiment is not limited to the following examples.

(a) Action of User
Walking
Running
Jumping
Stopping (b) Posture of User
Standing
Sitting
Lying (c) Transfer of User
Transfer by walking or running (on foot)
Transfer by bicycle
Transfer by train
Transfer by car
Transfer by bus
Transfer by escalator
(d) Daily Activity Depending on Stay Location
Shopping
Housekeeping
Working
Commuting Behavior of the user indicated by the behavior-recognition-result information corresponding to the reference apparatus according to the present embodiment is recognized on the basis of detection values and the like from the sensor included in the reference apparatus or the external sensor attached to the reference apparatus, for example. The action of the user in (a) is recognized on the basis of a direction and an amount of change in acceleration detected by the acceleration sensor, for example. The posture of the user in (b) is recognized on the basis of a direction and an amount of change in acceleration detected by the acceleration sensor, and the previously-recognized action of the user, for example. The transfer of the user in (c) is recognized on the basis of a position detected by a GPS device, map data, and an amount of change in acceleration detected by the acceleration sensor, for example. The daily activity depending on the stay location in (d) is recognized on the basis of a position detected by the GPS device, map data, time information, and schedule data of the user, for example.

The behavior-recognition-result information according to the present embodiment may be generated by the first information processing apparatus 100, or may be generated by the external apparatus of the first information processing apparatus 100. In the case where the external apparatus generates the behavior-recognition-result information, the first information processing apparatus 100 sets the behavior recognition mode by using the behavior-recognition-result information acquired from the external apparatus through communication, for example.

Hereinafter, details of an example of the behavior-recognition-mode setting process will be described while the case where the first information processing apparatus 100 sets the behavior recognition mode for the setting target apparatus on the basis of the status of the reference apparatus recognized in the process (1) (status recognition process) and the behavior-recognition-result information corresponding to the reference apparatus is mainly used as an example.

In addition, hereinafter, details of an example of the behavior-recognition-mode setting process will be described while the case where the first information processing apparatus 100 sets the behavior recognition mode for the second information processing apparatus 200 serving as the setting target apparatus is used as an example. Note that, as described above, the setting target apparatuses according to the present embodiment may be the reference apparatus and one or more second information processing apparatuses 200, for example. In other words, in the information processing system 1000 according to the first embodiment in FIG. 2, it is also possible for the first information processing apparatus 100 to set the behavior recognition mode for the first information processing apparatus serving as the reference apparatus and the second information processing apparatuses 200. In the case where the behavior recognition mode is set for the first information processing apparatus 100 serving as the reference apparatus, the first information processing apparatus 100 sets the behavior recognition mode for the first information processing apparatus 100 in a way similar to the case where the behavior recognition mode is set for the second information processing apparatuses 200, for example.

The first information processing apparatus 100 specifies, for example, the behavior recognition mode corresponding to the behavior-recognition-result information and the status of the reference apparatus recognized in the process (1) (status recognition process) by using setting information in which the status of the apparatus, behavior of the user, and the behavior recognition mode are associated with each other. In the case where the first information processing apparatus 100 sets the behavior recognition mode on the basis of the status of the reference apparatus recognized in the process (1) (status recognition process), it is also possible for the first information processing apparatus 100 to specify the behavior recognition mode corresponding to the status of the reference apparatus recognized in the process (1) (status recognition process) by using setting information in which the status of the apparatus and the behavior recognition mode are associated with each other, for example.

The first information processing apparatus 100 uses setting information read out from a storage unit (to be described later) included in the first information processing apparatus 100, a recording medium connected to the first information processing apparatus 100, and a recording medium included in an external apparatus having a communication function, for example. Examples of the setting information according to the present embodiment include a table and database.

Association between the status of the apparatus, the behavior of the user, and the behavior recognition mode in the setting information according to the present embodiment is set in advance, for example.

In addition, the association between the status of the apparatus, the behavior of the user, and the behavior recognition mode in the setting information according to the present embodiment may be updated on the basis of a user operation.

Examples of the user operation for updating the setting information according to the present embodiment include a user operation for directly updating the association between the status of the apparatus, the behavior of the user, and the behavior recognition mode. Since the association in the setting information according to the present embodiment is updated by the user operation for directly updating the association, it is possible for the user to set a desired behavior recognition mode for the setting target apparatus.

For example, the user operation for updating the setting information according to the present embodiment may be a user operation for indirectly updating the association between the status of the apparatus, the behavior of the user, and the behavior recognition mode. Examples of the user operation for indirectly updating the association include a feedback operation of the user of the setting target apparatus for a result of a process relating to behavior recognition in the setting target apparatus. For example, in the case where the feedback indicated by the feedback operation indicates that the result of the process relating to behavior recognition is not a desired result, the first information processing apparatus 100 changes the association between the status of the apparatus, the behavior of the user, and the behavior recognition mode in the setting information on the basis of frequency of the feedback, a level of the feedback, and the like.

When the behavior recognition mode corresponding to the behavior-recognition-result information, and the status of the reference apparatus recognized in the process (1) (status recognition process) are specified, the first information processing apparatus 100 sets the specified behavior recognition mode for the setting target apparatus.

FIGS. 3 to 6 are each an explanatory diagram illustrating an example of the process in the information processing method according to the present embodiment. FIGS. 3 to 6 each indicates an example of the behavior recognition mode set by the first information processing apparatus 100 for the second information processing apparatus 200, the second information processing apparatus 200 serving as the setting target apparatus. Association between the status of the apparatus, the behavior of the user, and the behavior recognition mode indicated in A in FIGS. 3 to 6 corresponds to an example of the association between the status of the apparatus, the behavior of the user, and the behavior recognition mode indicated by the setting information.

FIG. 3 illustrates an example of the behavior recognition modes set for the second information processing apparatuses 200 in the case where the first information processing apparatus 100 is a smartphone, and the second information processing apparatuses 200 serving as the setting target apparatuses are the wristband apparatus and the ankle-worn apparatus. FIG. 4 illustrates an example of the behavior recognition modes set for the second information processing apparatuses 200 in the case where the first information processing apparatus 100 is the clip type apparatus attached to ones waist, and the second information processing apparatuses 200 are the HMD and the apparatus hung around one's neck. FIG. 5 illustrates an example of the behavior recognition modes set for the second information processing apparatuses 200 in the case where the first information processing apparatus 100 is the clip type apparatus attached to ones waist, and the second information processing apparatuses 200 are the eyewear apparatus and the wristband apparatus. FIG. 6 illustrates an example of the behavior recognition modes set for the second information processing apparatuses 200 in the case where the first information processing apparatus 100 is a smartphone, and the second information processing apparatuses 200 are the ring apparatus, the necklace apparatus, and the eyewear apparatus.

For example, as illustrated in FIGS. 3 to 6, in the case where there are a plurality of the second information processing apparatuses 200 as the setting target apparatuses, the first information processing apparatus 100 sets a behavior recognition mode corresponding to each of the second information processing apparatuses 200 for each of the second information processing apparatuses 200.

The first information processing apparatus 100 carries out the above described process as the behavior-recognition-mode setting process to set the behavior recognition mode for the setting target apparatus.

Hereinafter, a specific example of the behavior-recognition-mode setting process according to the present embodiment will be described.

(2-1) First Example of Behavior-Recognition-Mode Setting Process

The first information processing apparatus 100 sets the same behavior recognition mode for the plurality of the second information processing apparatus 200 on the basis of the "status of the reference apparatus recognized in the process (1) (status recognition process) or the "behavior-recognition-result information and the recognized status of the reference apparatus".

Figure 7:
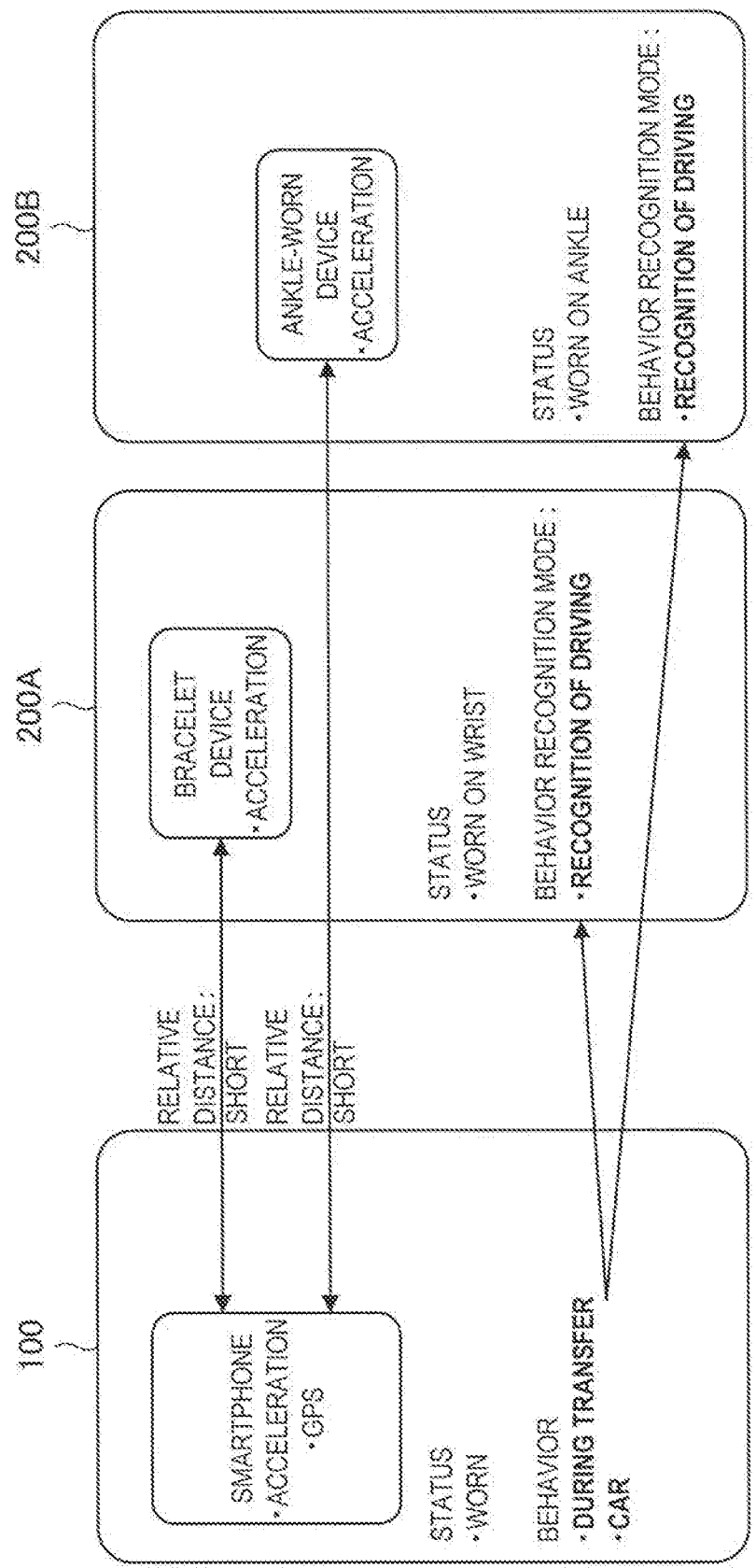
FIG. 7 is an explanatory diagram illustrating a first example of a behavior-recognition-mode setting process in an information processing method according to the present embodiment.

FIG. 7 is an explanatory diagram illustrating a first example of the behavior-recognition-mode setting process in the information processing method according to the present embodiment. FIG. 7 illustrates a smartphone as the first information processing apparatus 100 serving as the reference apparatus, and illustrates a bracelet apparatus and an ankle-worn apparatus as the second information processing apparatuses 200A and 200B that are the setting target apparatus. In addition, in the example illustrated in FIG. 7, the first information processing apparatus 100 sets a behavior recognition mode for "recognition of driving" for each of the second information processing apparatuses 200A and 200B.

As illustrated in FIG. 7, since the first information processing apparatus 100 sets the behavior recognition mode for "recognition of driving" for each of the second information processing apparatuses 200A and 200B, it is possible for the second information processing apparatuses 200A and 200B to recognize behavior relating to the "recognition of driving" in the information processing system 1000.

(2-2) Second Example of Behavior-Recognition-Mode Setting Process

The first information processing apparatus 100 sets a behavior recognition mode for each of the second information processing apparatuses 200 on the basis of the "status of the reference apparatus recognized in the process (1) (status recognition process)" or the "behavior-recognition-result information and the recognized status of the reference apparatus".

Figure 8:
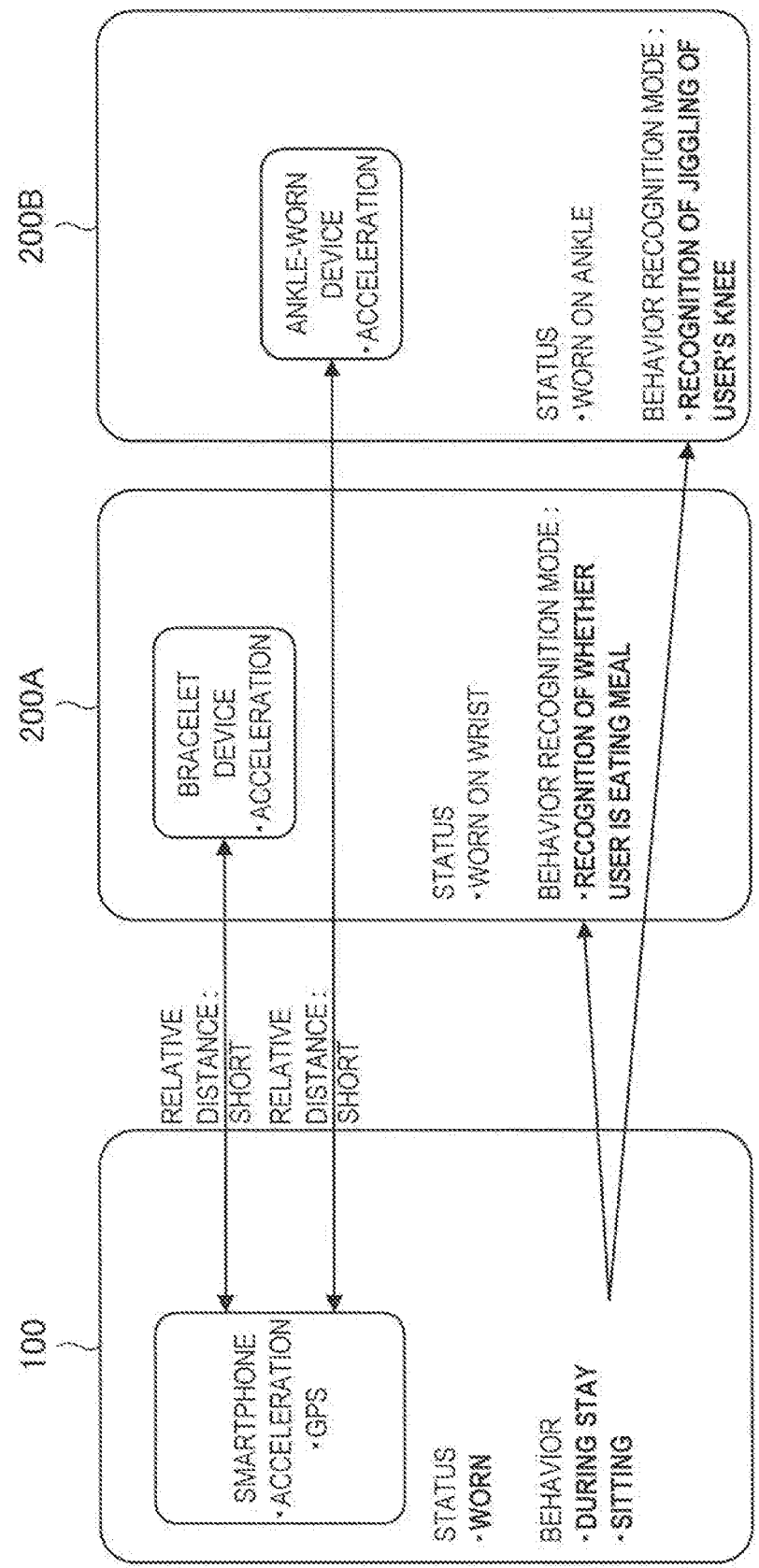
FIG. 8 is an explanatory diagram illustrating a second example of a behavior-recognition-mode setting process in an information processing method according to the present embodiment.

FIG. 8 is an explanatory diagram illustrating a second example of the behavior-recognition-mode setting process in the information processing method according to the present embodiment. FIG. 8 illustrates a smartphone as the first information processing apparatus 100 serving as the reference apparatus, and illustrates a bracelet apparatus and an ankle-worn apparatus as the second information processing apparatuses 200A and 200B that are the setting target apparatus. In addition, in the example illustrated in FIG. 8, the first information processing apparatus 100 sets a behavior recognition mode for "recognition of whether the user is eating a meal" for the second information processing apparatus 200A, and sets a behavior recognition mode for "recognition of jiggling of the user's knee" for the second information processing apparatus 200B.

As illustrated in FIG. 8, since the first information processing apparatus 100 sets the corresponding behavior recognition mode for each of the second information processing apparatuses 200A and 200B, it is possible to recognize behavior different for each of the second information processing apparatuses 200A and 200B in the information processing system 1000. Sometimes the same behavior is recognized for each of the second information processing apparatuses 200 as a result of setting of behavior recognition modes corresponding to each of the second information processing apparatuses 200 by the first information processing apparatus 100.

(2-3) Third Example of Behavior-Recognition-Mode Setting Process

The first information processing apparatus 100 sets a behavior recognition mode on the basis of the "status of the reference apparatus recognized in the process (1) (status recognition process)" or the "behavior-recognition-result information and the recognized status of the reference apparatus". Thereby, behavior recognition modes are selectively set for one or more of the plurality of the second information processing apparatuses 200 in the information processing system 1000.

FIG. 9 is an explanatory diagram illustrating a third example of the behavior-recognition-mode setting process in the information processing method according to the present embodiment. In an example A in FIG. 9, the first information processing apparatus 100 sets a behavior recognition mode for "sleep detection" for the second information processing apparatus 200A, but does not set any behavior recognition mode for the second information processing apparatus 200B. In an example B in FIG. 9, the first information processing apparatus 100 sets a behavior recognition mode for "recognition of cadence" for the second information processing apparatus 200B, but does not set any behavior recognition mode for the second information processing apparatus 200A. The examples A and B in FIG. 9 each illustrates a smartphone as the first information processing apparatus 100 serving as the reference apparatus, and illustrates a bracelet apparatus and an ankle-worn apparatus as the second information processing apparatuses 200A and 200B that are the setting target apparatus.

As illustrated in the examples A and B in FIG. 9, it is possible for the first information processing apparatus 100 to set a behavior recognition mode for one of the second information processing apparatuses 200A and 200B.

(2-4) Fourth Example of Behavior-Recognition-Mode Setting Process

The first information processing apparatus 100 sets a behavior recognition mode for the setting target apparatus on the basis of a relative distance between the reference apparatus and the second information processing apparatus 200 (an apparatus other than the reference apparatus among setting target apparatuses) in addition to the "status of the reference apparatus recognized in the process (1) (status recognition process)" or the "behavior-recognition-result information and the recognized status of the reference apparatus".

More specifically, for example, in the case where it is determined that the relative distance between the reference apparatus and the second information processing apparatus 200 is far, the first information processing apparatus 100 sets, for the second information processing apparatus 200, a behavior recognition mode in which a process relating to behavior recognition is not carried out. The behavior recognition mode in which the process relating to behavior recognition is not carried out according to the present embodiment includes one or both of a setting in which sensors for recognizing behavior is not activated (including a setting for setting the sensors to be in a sleep mode) and a setting for stopping execution of the process relating to behavior recognition.

The first information processing apparatus 100 sets a behavior recognition mode for the second information processing apparatus 200 on the basis of the "status of the reference apparatus recognized in the process (1) (status recognition process)" or the "behavior-recognition-result information and the recognized status of the reference apparatus" in the case where it is determined that the relative distance between the reference apparatus and the second information processing apparatus 200 is short.

Here, the first information processing apparatus 100 determines that the relative distance between the reference apparatus and the second information processing apparatus 200 is long in the case where communication between the reference apparatus and the second information processing apparatus 200 is not established, for example. Alternatively, the first information processing apparatus 100 determines that the relative distance between the reference apparatus and the second information processing apparatus 200 is short in the case where communication between the reference apparatus and the second information processing apparatus 200 is established, for example.

Alternatively, in the case where the relative distance between the reference apparatus and the second information processing apparatus 200 is obtained using any method for measuring the distance such as a method for estimating the distance on the basis of a difference between time when a transmission signal has been transmitted and time when an answer signal to the transmission signal has been received, the first information processing apparatus 100 determines that the relative distance between the reference apparatus and the second information processing apparatus 200 is long when the relative distance between the reference apparatus and the second information processing apparatus 200 is greater than a threshold (or greater than or equal to the threshold. The same applies to below), for example. Alternatively, in the case where the relative distance between the reference apparatus and the second information processing apparatus 200 is obtained using any method for measuring the distance, the first information processing apparatus 100 determines that the relative distance between the reference apparatus and the second information processing apparatus 200 is short when the relative distance between the reference apparatus and the second information processing apparatus 200 is less than or equal to a threshold (or less than the threshold. The same applies to below), for example.

Here, in the case where the first information processing apparatus 100 is the reference apparatus, the first information processing apparatus 100 carries out the behavior-recognition-mode setting process according to the first example on the basis of whether or not the first information processing apparatus 100 can communicate with the second information processing apparatus 200 or on the basis of an estimated distance between the first information processing apparatus 100 and the second information processing apparatus 200, for example.

Alternatively, in the case where the reference apparatus is an external apparatus different from the first information processing apparatus 100, the first information processing apparatus 100 carries out the behavior-recognition-mode setting process according to the first example on the basis of information (for example, flag) indicating whether or not communication with the second information processing apparatus 200 can be established or on the basis of information indicating an estimated distance between the external apparatus and the second information processing apparatus 200. Such information has been acquired from the external apparatus.

Figure 10:
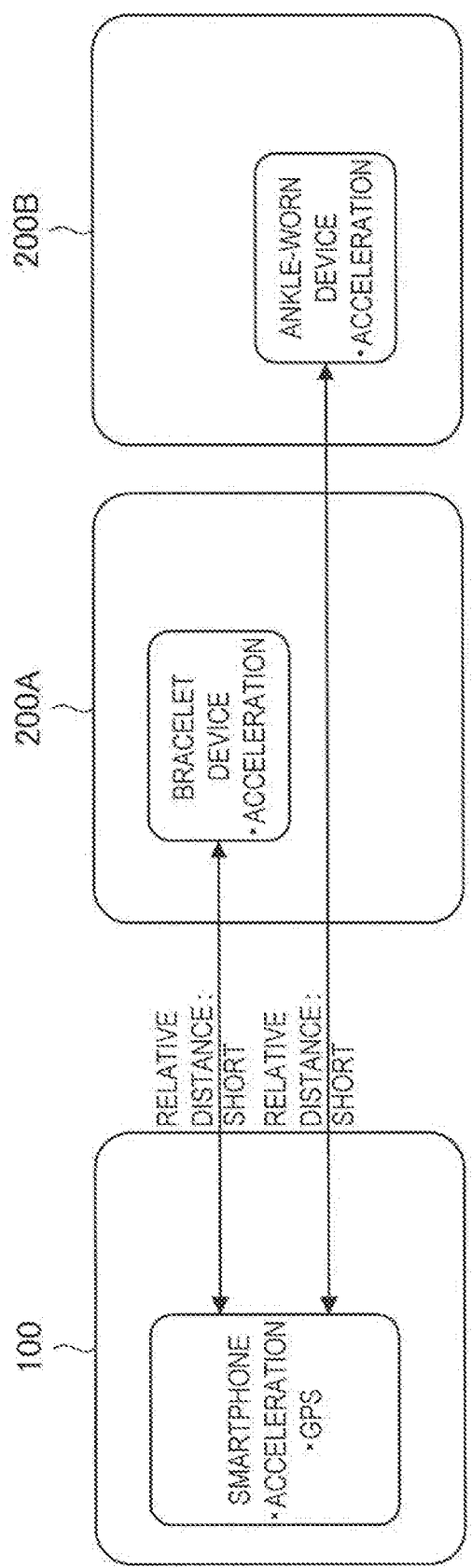
FIG. 10 is an explanatory diagram illustrating a fourth example of a behavior-recognition-mode setting process in an information processing method according to the present embodiment.

FIG. 10 is an explanatory diagram illustrating a fourth example of the behavior-recognition-mode setting process in the information processing method according to the present embodiment. FIG. 10 illustrates a smartphone as the first information processing apparatus 100 serving as the reference apparatus, and illustrates a bracelet apparatus and an ankle-worn apparatus as the second information processing apparatuses 200A and 200B that are the setting target apparatus.

The first information processing apparatus 100 determines a relative distance from each of the second information processing apparatus 200A and the second information processing apparatus 200B. In the example in FIG. 10, a relative distance between the first information processing apparatus 100 and the second information processing apparatus 200A is short, and a relative distance between the first information processing apparatus 100 and the second information processing apparatus 200B is also short. Therefore, in the example in FIG. 10, the first information processing apparatus 100 sets a behavior recognition mode based on the "status of the reference apparatus recognized in the process (1) (status recognition process)" or the "behavior-recognition-result information and the recognized status of the reference apparatus", for each of the second information processing apparatuses 200A and 200B.

(2-5) Fifth Example of Behavior-Recognition-Mode Setting Process

The first information processing apparatus 100 sets a behavior recognition mode on the basis of the "status of the reference apparatus recognized in the above described process (1) (status recognition process)". In the case where the status of the reference apparatus recognized in the process (1) (status recognition process) is the "status where the apparatus is left", the first information processing apparatus 100 sets a behavior recognition mode corresponding to a location where the reference apparatus is left, for the second information processing apparatus 200.

In the case where the status of the reference apparatus recognized in the process (1) (status recognition process) is the "status where the apparatus is left", the first information processing apparatus 100 transmits information indicating the behavior recognition mode according to the present embodiment to the second information processing apparatus 200, the information including an "order to carry out the process relating to behavior recognition when it has been determined that a relative distance between the reference apparatus and the second information processing apparatus 200 is long".

Figure 11:
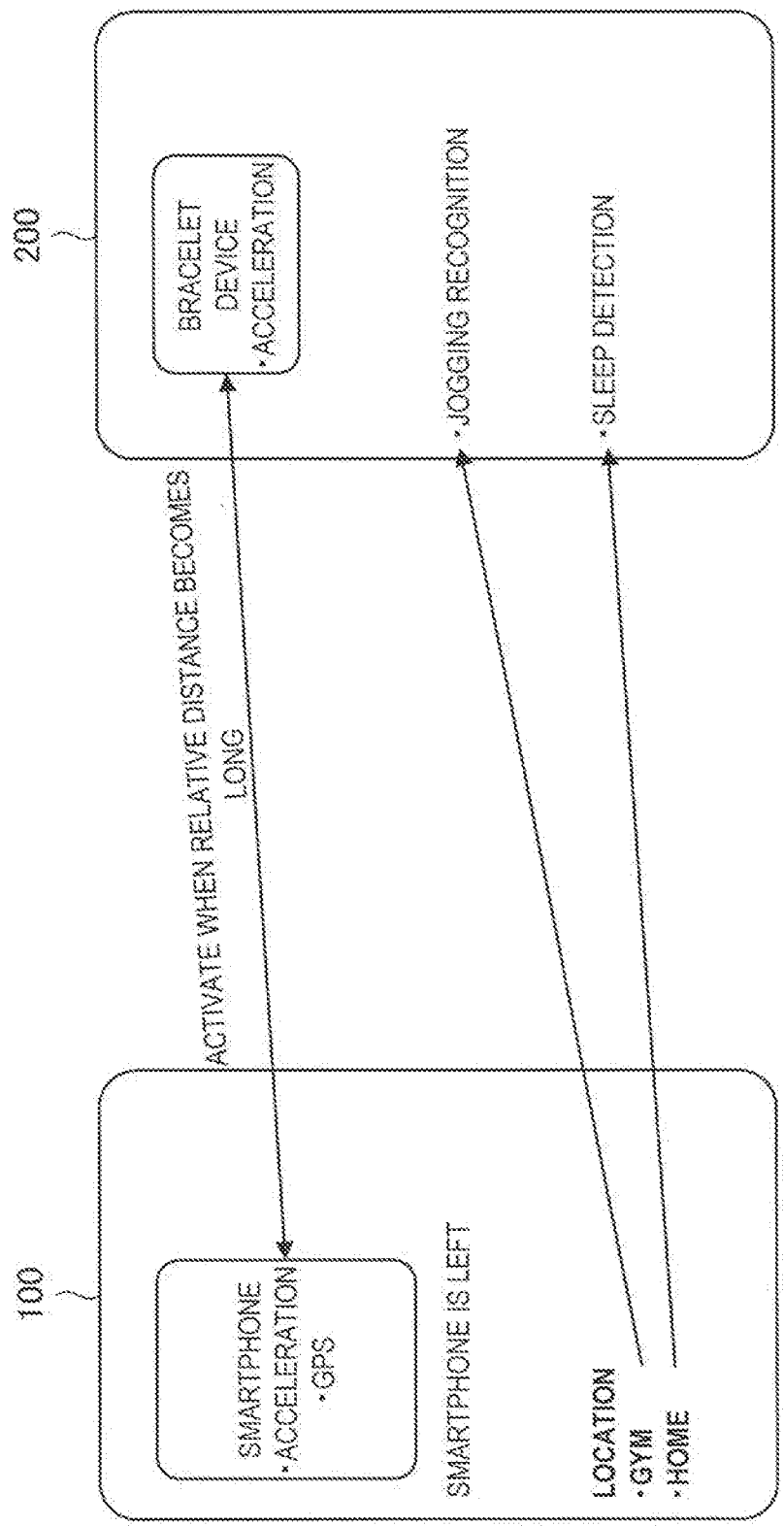
FIG. 11 is an explanatory diagram illustrating a fifth example of a behavior-recognition-mode setting process in an information processing method according to the present embodiment.

FIG. 11 is an explanatory diagram illustrating a fifth example of the behavior-recognition-mode setting process in the information processing method according to the present embodiment. FIG. 11 illustrates a smartphone as the first information processing apparatus 100 serving as the reference apparatus, and illustrates a bracelet apparatus as the second information processing apparatus 200 that is the setting target apparatus. In FIG. 11, the first information processing apparatus 100 sets a behavior recognition mode for "recognition of jogging" or a behavior recognition mode for "detection of sleeping" for the second information processing apparatus 200 in accordance with a location where the first information processing apparatus 100 serving as the reference apparatus is left.

In the example in FIG. 11, for example, the second information processing apparatus 200 determines a relative distance between the second information processing apparatus 200 and the first information processing apparatus 100 serving as the reference apparatus, in a way similar to the case of the first information processing apparatus 100 in (2-4) described above. Subsequently, in the case where it has been determined that the relative distance between the second information processing apparatus 200 and the first information processing apparatus 100 is long, the second information processing apparatus 200 carries out the process relating to behavior recognition according to the setting relating to the behavior recognition indicated by the behavior recognition mode.

Note that, the information indicating the behavior recognition mode transmitted from the first information processing apparatus 100 in the behavior-recognition-mode setting process according to the fifth example is not limited to the information indicating the behavior recognition mode including the order to carry out the process relating to behavior recognition when it has been determined that a relative distance between the reference apparatus and the second information processing apparatus 200 is long.

For example, the first information processing apparatus 100 may transmit, to the second information processing apparatus 200, information indicating a behavior recognition mode according to the present embodiment, the information including a setting of a sensor for acquiring position information such as a GPS device, and an order to carry out the process relating to behavior recognition according to a position indicated by the position information.

(2-6) Sixth Example of Behavior-Recognition-Mode Setting Process

The first information processing apparatus 100 sets a behavior recognition mode on the basis of the "status of the reference apparatus recognized in the process (1) (status recognition process) or the "behavior-recognition-result information and the recognized status of the reference apparatus". In the case where the status of the reference apparatus recognized in the process (1) (status recognition process) is the "status where the apparatus is left", the first information processing apparatus 100 transmits information indicating the behavior recognition mode according to the present embodiment to the second information processing apparatus 200, the information including a "plurality of behavior recognition modes corresponding to relative distances between the reference apparatus and the second information processing apparatuses 200" and an "order to carry out the process relating to behavior recognition corresponding to the relative distances between the reference apparatus and the second information processing apparatuses 200".

Figure 12:
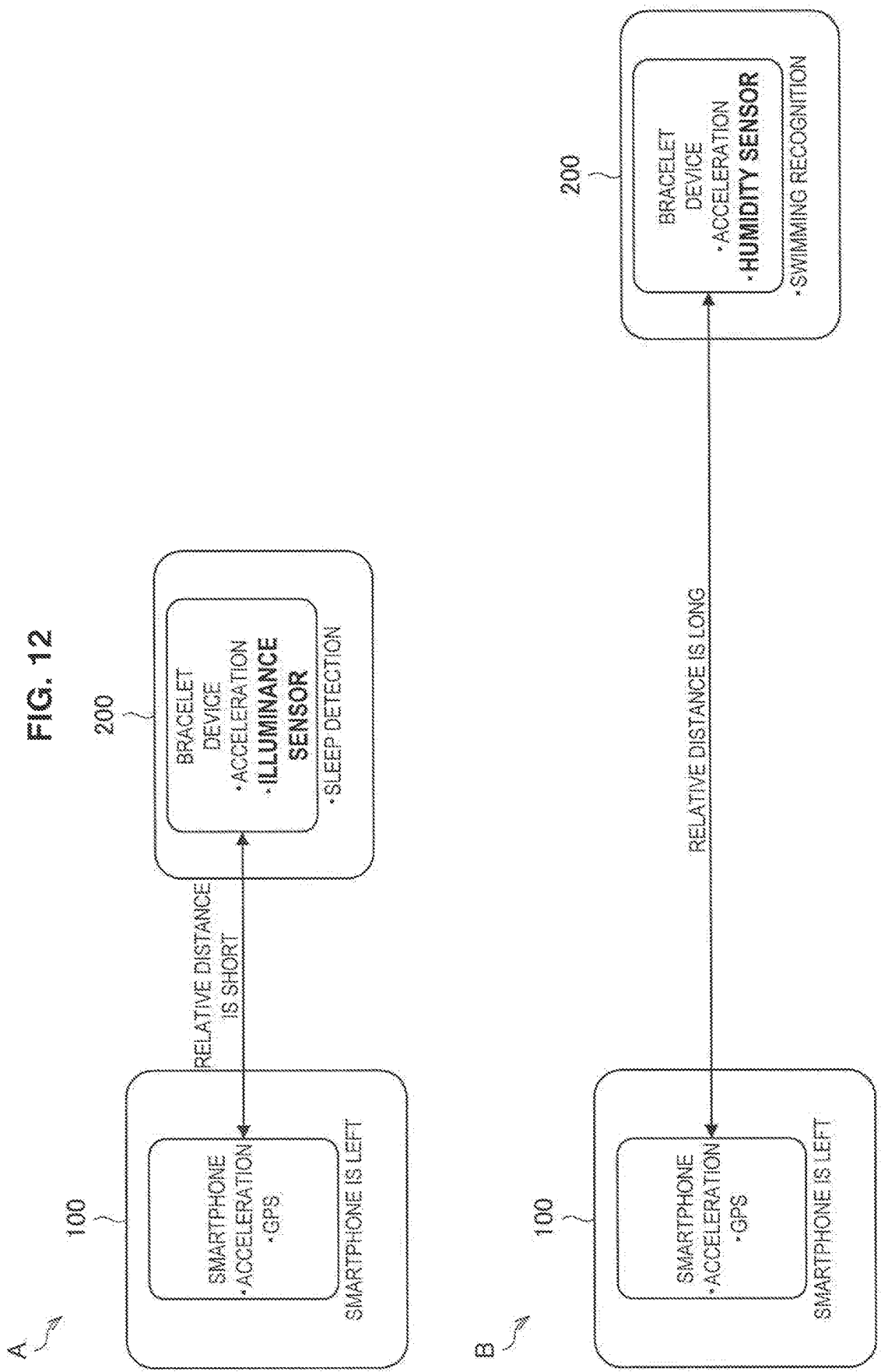
FIG. 12 is an explanatory diagram illustrating a sixth example of a behavior-recognition-mode setting process in an information processing method according to the present embodiment.

FIG. 12 is an explanatory diagram illustrating a sixth example of the behavior-recognition-mode setting process in the information processing method according to the present embodiment. An example A in FIG. 12 illustrates the case where the relative distance between the first information processing apparatus 100 serving as the reference apparatus and the second information processing apparatus 200 that is the setting target apparatus is short. An example B in FIG. 12 illustrates the case where the relative distance between the first information processing apparatus 100 and the second information processing apparatus 200 is long. FIG. 12 illustrates a smartphone as the first information processing apparatus 100, and illustrates a bracelet apparatus as the second information processing apparatus 200. In addition, FIG. 12 illustrates an example in which the first information processing apparatus 100 sets, for the second information processing apparatus 200, the behavior recognition mode for "detection of sleep" corresponding to the case where the relative distance between the first information processing apparatus 100 and the second information processing apparatus 200 is short, and an example in which the first information processing apparatus 100 sets, for the second information processing apparatus 200, the behavior recognition mode for "recognition of swimming" corresponding to the case where the relative distance is short.

In the example in FIG. 12, the second information processing apparatus 200 determines a relative distance between the second information processing apparatus 200 and the first information processing apparatus 100 serving as the reference apparatus, in a way similar to the case of the first information processing apparatus 100 in (2-4) described above. Subsequently, in the case where it has been determined that the relative distance between the second information processing apparatus 200 and the first information processing apparatus 100 is short, the second information processing apparatus 200 carries out the process for detecting sleeping in which detection values from an illuminance sensor are used in addition to detection values from the acceleration sensor, as the process relating to behavior recognition, for example (example A in FIG. 12). Alternatively, in the case where it has been determined that the relative distance between the second information processing apparatus 200 and the first information processing apparatus 100 is long, the second information processing apparatus 200 carries out the process for recognizing swimming in which detection values from a humidity sensor are used in addition to the acceleration sensor, as the process relating to behavior recognition, for example (example B in FIG. 12).

In the above examples, the first information processing apparatus 100 sets, for the setting target apparatuses, the plurality of behavior recognition modes corresponding to the relative distances between the reference apparatus and the second information processing apparatuses 200. However, the behavior-recognition-mode setting process according to the present embodiment is not limited to the above described examples.

For example, it is also possible for the first information processing apparatus 100 to set the plurality of behavior recognition modes corresponding to any condition such as whether or not detection values from any one or more sensors exceed thresholds. In addition, it is also possible for the first information processing apparatus 100 to set the plurality of behavior recognition modes corresponding to combinations of a plurality of conditions, for example.

In the master-slave type information processing system 1000, the first information processing apparatus 100 sets the behavior recognition mode for the second information processing apparatus 200 serving as the setting target apparatus by carrying out the process (1) (status recognition process) and the process (2) (behavior-recognition-mode setting process).

Accordingly, since the first information processing apparatus 100 carries out the process (1) (status recognition process) and the process (2) (behavior-recognition-mode setting process) as the processes in the information processing method according to the present embodiment, it is possible to realize the master-slave type information processing system capable of recognizing behavior of a user with a higher accuracy.

[2] Process in Second Information Processing Apparatus 200

In the information processing system 1000, the second information processing apparatus 200 carries out the process relating to behavior recognition according to the setting relating to the behavior recognition configured on the basis of information indicating a behavior recognition mode.

More specifically, for example, the second information processing apparatus 200 carries out the process relating to behavior recognition by carrying out (i) a setting process and (ii) an execution process.

(i) Setting Process

The second information processing apparatus 200 configures a setting of behavior recognition on the basis of information indicating the acquired behavior recognition mode.

Examples of the setting configured by the second information processing apparatus 200 include a setting of whether or not to use a sensor included in the second information processing apparatus 200 or a sensor connected to the second information processing apparatus 200, and a setting of parameters of the sensor. In addition, the examples of the setting configured by the second information processing apparatus 200 include a setting of a type of a feature amount to be used for the behavior recognition among the detection values from the sensor, and a setting of an algorithm and model data to be used for the process for behavior recognition. In addition, the setting configured by the second information processing apparatus 200 may be a combination of the above described various types of settings.

(ii) Execution Process

The second information processing apparatus 200 carries out a process relating to behavior recognition according to the setting of the behavior recognition configured in the process (i) (setting process).

As described in (2-5) about the behavior-recognition-mode setting process according to the fifth example and in (2-6) about the behavior-recognition-mode setting process according to the fifth example, the second information processing apparatus 200 may carry out the process relating to behavior recognition on the basis of the relative distance from the reference apparatus or the position of the own apparatus, for example.

The second information processing apparatus 200 carries out the process (i) (setting process) and the process (ii) (execution process), and carries out the process relating to behavior recognition according to the behavior recognition mode set by the first information processing apparatus 100 to recognize behavior of a user. Accordingly, since the second information processing apparatus carries out the process (i) (setting process) and the process (ii) (execution process), it is possible to realize the master-slave type information processing system capable of recognizing behavior of a user with a higher accuracy.

[3] Configurations of First Information Processing Apparatus 100 and Second Information Processing Apparatus 200

Next, an example of the configurations of the first information processing apparatus 100 and the second information processing apparatus 200 that constitute the information processing system 1000 according to the first embodiment will be described.

[3-1] Example of Configuration of First Information Processing Apparatus 100

Figure 13:
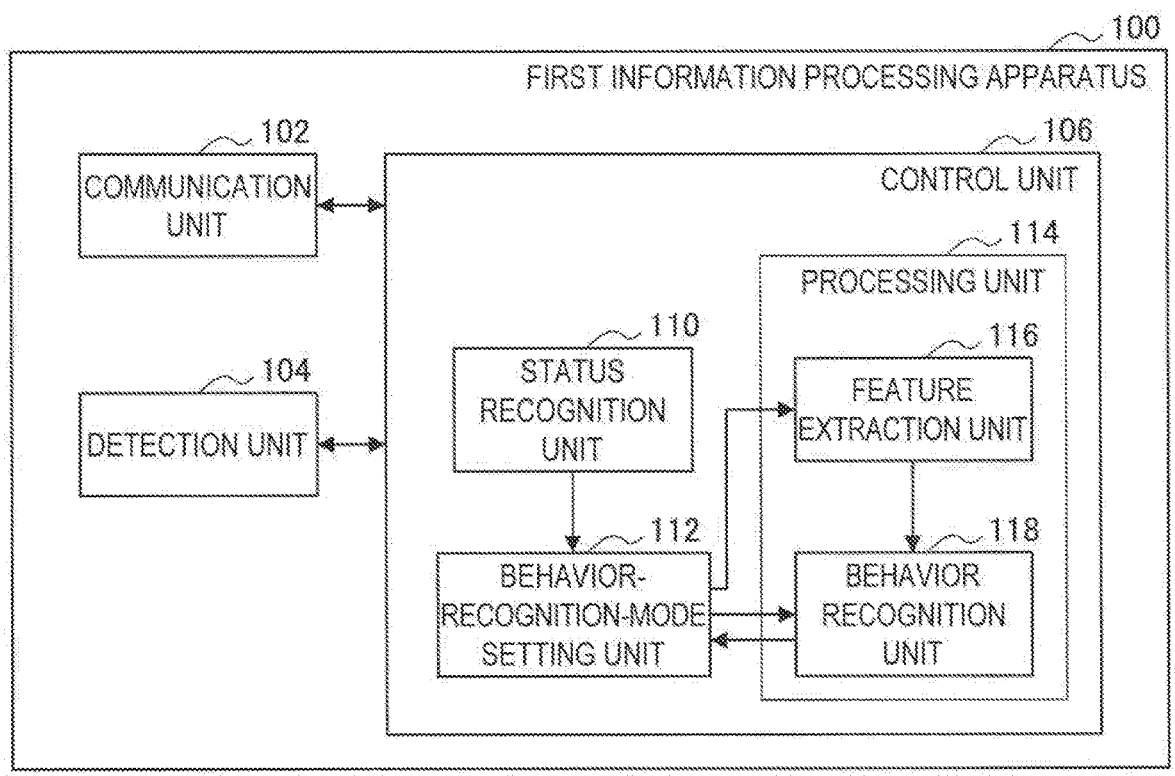
FIG. 13 is a block diagram illustrating an example of a configuration of a first information processing apparatus according to the present embodiment, the first information processing apparatus constituting an information processing system according to the first embodiment.

FIG. 13 is a block diagram illustrating an example of the configuration of the first information processing apparatus 100 according to the present embodiment, the first information processing apparatus constituting the information processing system 1000 according to the first embodiment. The first information processing apparatus 100 includes a communication unit 102, a detection unit 104, and a control unit 106, for example.

In addition, the first information processing apparatus 100 may include read only memory (ROM) (not illustrated), random access memory (RAM) (not illustrated), a storage unit (not illustrated), an operation unit (not illustrated) operated by a user, and a display unit (not illustrated) for displaying various screens on a display screen, for example. In the first information processing apparatus 100, the structural elements are connected via a bus serving as a data transmission channel, for example.

The ROM (not illustrated) stores control data used by the control unit 106 such as programs and operation parameters. The RAM (not illustrated) temporarily stores programs and the like executed by the control unit 106.

The storage unit (not illustrated) is a storage mechanism included in the first information processing apparatus 100. For example, the storage unit stores various kinds of data such as an application and data relating to the information processing method according to the present embodiment like setting information according to the present embodiment. Examples of the storage unit (not illustrated) include a magnetic recording medium such as a hard disk, and non-volatile memory such as flash memory. The storage unit (not illustrated) may be detachably attached to the first information processing apparatus 100.

Examples of the operation unit (not illustrated) include an operation input device (to be described later). Examples of the display unit (not illustrated) include a display device (to be described later).

[Hardware Configuration Example of First Information Processing Apparatus 100]

Figure 14:
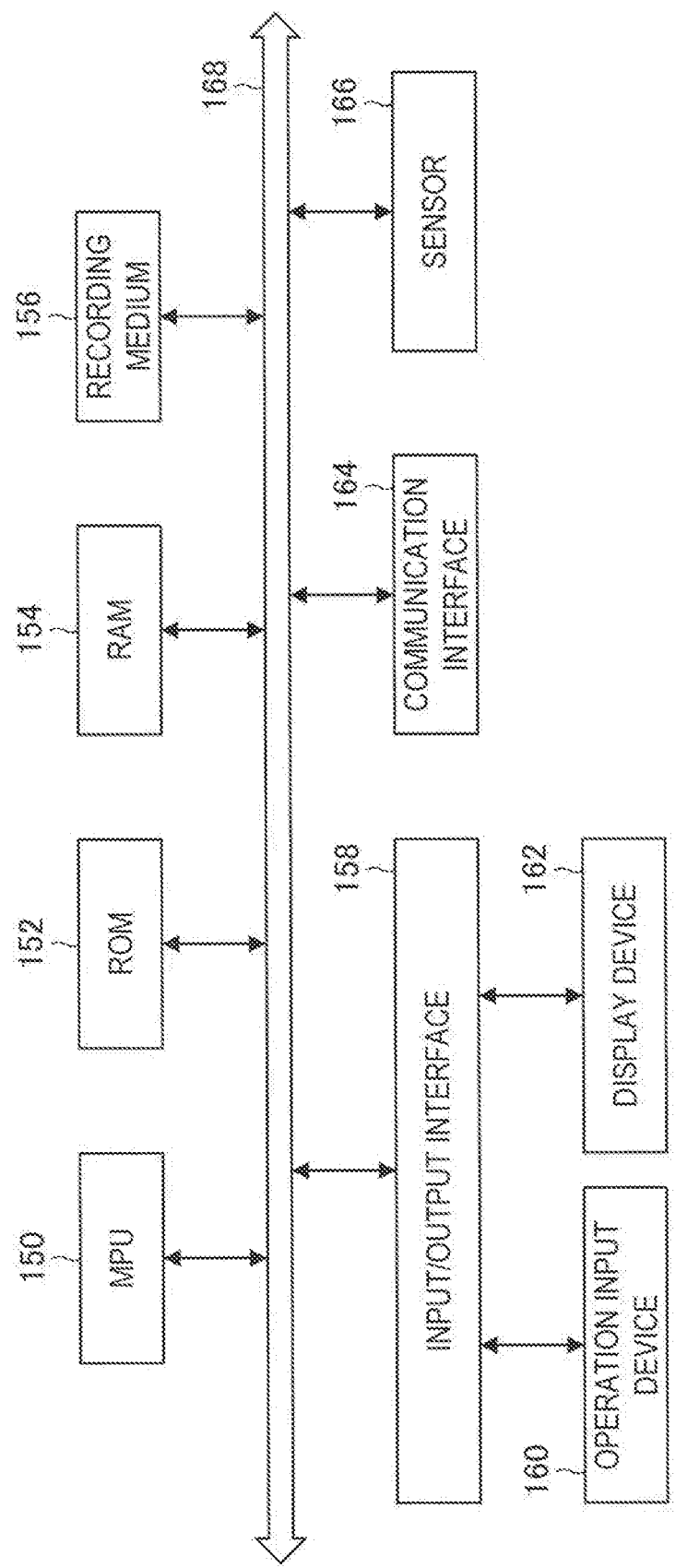
FIG. 14 is an explanatory diagram illustrating an example of a hardware configuration of a first information processing apparatus according to the present embodiment, the first information processing apparatus constituting an information processing system according to the first embodiment.

FIG. 14 is an explanatory diagram illustrating an example of a hardware configuration of the first information processing apparatus 100 according to the present embodiment, the first information processing apparatus 100 constituting the information processing system 1000 according to the first embodiment. The first information processing apparatus 100 includes an MPU 150, ROM 152, RAM 154, a recording medium 156, an input/output interface 158, an operation input device 160, a display device 162, a communication interface 164, and a sensor 166, for example. In the first information processing apparatus 100, the structural elements are connected via a bus 168 serving as a data transmission channel, for example.

For example, the MPU 150 is constituted of various kinds of processing circuits and a processor constituted of an operational circuit such as a micro processing unit (MPU). The MPU 150 functions as the control unit 106 that controls the entire first information processing apparatus 100. In addition, in the first information processing apparatus 100, the MPU 150 also serves as a status recognition unit 110, a behavior-recognition-mode setting unit 112, and a processing unit 114 that will be described later, for example.

The ROM 152 stores control data such as operation parameters, programs, and the like used by the MPU 150. The RAM 154 temporarily stores programs and the like executed by the MPU 150, for example.

The recording medium 156 functions as the storage unit (not illustrated). For example, the recording medium 156 stores various kinds of data such as an application and data relating to the information processing method according to the present embodiment like setting information according to the present embodiment. Examples of the recording medium 156 include a magnetic recording medium such as a hard disk, and nonvolatile memory such as flash memory. The recording medium 156 may be detachably attached to the first information processing apparatus 100.

The input/output interface 158 connects the operation input device 160 and the display device 162, for example. The operation input device 160 functions as the operation unit (not illustrated), and the display device 162 functions as the display unit (not illustrated). Examples of the input/output interface 158 include a universal serial bus (USB) terminal, a digital visual interface (DVI) terminal, a High-Definition Multimedia Interface (HDMI) (registered trademark) terminal, and various kinds of processing circuits.

The operation input device 160 is installed at the surface of the first information processing apparatus 100, and connected to the input/output interface 158 in the first information processing apparatus 100, for example. Examples of the operation input device 160 include a button, arrow keys, rotary type selectors such as jog dials, and a combination thereof.

The display device 162 is installed at the surface of the first information processing apparatus 100, and connected to the input/output interface 158 in the first information processing apparatus 100, for example. Examples of the display device 162 include a liquid crystal display, and an organic electro-luminescence display (also referred to as an organic light emitting diode (OLED) display).

Of course, the input/output interface 158 is capable of being connected to an external device such as an external operation input device (for example, keyboard or mouse), an external display device, or an external sensor each of which serves as an external apparatus of the first information processing apparatus 100. In addition, the display device 162 may be a device capable of displaying and being operated by a user such as a touchscreen.

The communication interface 164 is a communication mechanism included in the first information processing apparatus 100, and functions as the communication unit 102 for communicating with the second information processing apparatus 200 or an external apparatus such as the external reference apparatus in a wired/wireless manner via a network (or directly). Here, examples of the communication interface 164 include IEEE 802.11 port and transmission/reception circuit (wireless communication), IEEE 802.15.1 port and transmission/reception circuit (wireless communication), communication antenna and RF circuit (wireless communication), local area network (LAN) terminal and transmission/reception circuit (wired communication), and the like. In addition, examples of the network according to the present embodiment may include a wired network such as LAN or WAN (Wide Area Network), a wireless network such as wireless WAN (WWAN; Wireless Wide Area Network) via a base station or wireless LAN (WMAN; Wireless Local Area Network), Internet using a communication protocol such as TCP/IP (Transmission Control Protocol/Internet Protocol), and the like.

The sensor 166 is a mechanism for detecting statuses of apparatuses included in the first information processing apparatus 100, and functions as the detection unit 104. Examples of the sensor 166 include any sensors to be used for the process for behavior recognition of a user, such as an acceleration sensor, a GPS device, a gyro sensor, an atmospheric pressure sensor, a proximity sensor, or a biosensor. The sensor 166 may be a sensor group including a plurality of sensors.

The first information processing apparatus 100 carries out the process relating to the information processing method according to the present embodiment by the configuration illustrated in FIG. 14, for example. Note that, the hardware configuration of the first information processing apparatus 100 according to the present embodiment is not limited to the configuration in FIG. 14.

For example, when the first information processing apparatus 100 serves as the reference apparatus, the first information processing apparatus 100 does not have to include the sensor 166 in the case where the first information processing apparatus 100 carries out the process (1) (status recognition process) on the basis of information on a status of an apparatus indicating a detection result from the external sensor connected to the first information processing apparatus 100. Alternatively, when the first information processing apparatus 100 does not serve as the reference apparatus, the first information processing apparatus 100 does not have to include the sensor 166 in the case where the first information processing apparatus 100 carries out the process (1) (status recognition process) on the basis of acquired information on a status of an apparatus, for example.

In addition, for example, in the case where the first information processing apparatus 100 communicates with the external apparatus via a connected external communication device, the first information processing apparatus 100 does not have to include the communication interface 164. In addition, the information processing apparatus 100 may be configured not to include the recording medium 156, the operation device 160, or the display device 162.

With reference to FIG. 13 again, the example of the configuration of the first information processing apparatus 100 will be described. The communication unit 102 is a communication mechanism included in the first information processing apparatus 100, and communicates with the second information processing apparatus 200 or the external apparatus such as the external reference apparatus in a wired/wireless manner via a network (or directly). The communication performed by the communication unit 102 is controlled by the control unit 106, for example.

Examples of the communication unit 102 include a communication antenna, an RF circuit, a LAN terminal, and a transmission/reception circuit. However, the communication unit 102 is not limited thereto. For example, the communication unit 102 may have a configuration corresponding to any standard that enables communication such as a USB terminal or the transmission/reception circuit, or any configuration capable of communicating with the external apparatus via the network.

The detection unit 104 is a mechanism for detecting statuses of apparatuses included in the first information processing apparatus 100, and outputs a detection result of the status of the apparatus. The detection value output from the detection unit 104 corresponds to information on the status of the apparatus. Examples of the detection unit 104 include any sensors to be used for the process for behavior recognition of a user, such as an acceleration sensor or a GPS device. The detection unit 104 may be constituted of a sensor group including a plurality of sensors.

The control unit 106 is constituted of the MPU or the like and serves to control the entire first information processing apparatus 100, for example. In addition, the control unit 106 includes the status recognition unit 100, the behavior-recognition-mode setting unit 112, and the processing unit 114 for example, and serves to lead the process relating to the information processing method according to the present embodiment.

The control unit 106 may further include a communication control unit (not illustrated) for controlling communication in the communication unit 102, for example. The communication control unit (not illustrated) controls exchange of various kinds of information. The function of the communication control unit (not illustrated) may be carried out by another structural element such as the communication unit 102.

The status recognition unit 110 has a function of leading the process (1) (status recognition process) to recognize a status of the reference apparatus on the basis of information on a status of an apparatus.

For example, in the case where the first information processing apparatus 100 serves as the reference apparatus, the status recognition unit 110 recognizes a status of the reference apparatus on the basis of information on a status of an apparatus corresponding to a detection result output from the detection unit 104, or on the basis of information on a status of an apparatus corresponding to a user operation performed on the operation unit (not illustrated). Alternatively, in the case where the first information processing apparatus 100 does not serve as the reference apparatus, the status recognition unit 110 recognizes a status of the reference apparatus on the basis of information on a status of an apparatus corresponding to the reference apparatus, the information having been received from the communication unit 102, for example.

The behavior-recognition-mode setting unit 112 has a function of leading the process (2) (behavior-recognition-mode setting process) to set a behavior recognition mode for a setting target apparatus on the basis of the status of the reference apparatus recognized by the status recognition unit 110.

More specifically, for example, the behavior-recognition-mode setting unit 112 carries out any one of the behavior-recognition-mode setting process according to the first example described in (2-1) to the behavior-recognition-mode setting process according to the sixth example described in (2-6), so as to set a behavior recognition mode for the second information processing apparatus 200 serving as the setting target apparatus. In addition, for example, the behavior-recognition-mode setting unit 112 may carry out a plurality of combinable processes such as "the behavior-recognition-mode setting process according to the first example described in (2-1) and the behavior-recognition-mode setting process according to the fifth example described in (2-5)" or "the behavior-recognition-mode setting process according to the first example described in (2-1) and the behavior-recognition-mode setting process according to the sixth example described in (2-6)".

In the case where the first information processing apparatus 100 serves as the reference apparatus, the behavior-recognition-mode setting unit 112 sets its own apparatus (first information processing apparatus 100) as the setting target apparatus, and sets the behavior recognition mode for the own apparatus. In the case where the behavior recognition mode is set for the own apparatus, the behavior-recognition-mode setting unit 112 configures one or more of a setting of the detection unit 104, a setting of a feature extraction unit 116 (to be described later), and a setting of a behavior recognition unit 118 (to be described later).

In the case where the behavior recognition mode is set for the own apparatus, the process of the behavior-recognition-mode setting unit 112 corresponds to the process (i) (setting process) in the second information processing apparatus 200. Specifically, as the setting of the detection unit 104, the behavior-recognition-mode setting unit 112 configures a setting of whether a sensor constituting the detection unit 104 is used, or a setting of a parameter of the sensor, for example. As the setting of the feature extraction unit 116, the behavior-recognition-mode setting unit 112 configures a setting of a type of a feature amount to be used for behavior recognition among detection results from the detection unit 104, for example. As the setting of the behavior recognition unit 118, the behavior-recognition-mode setting unit 112 configures a setting of an algorithm and model data to be used for the process for behavior recognition, for example.

For example, the processing unit 114 includes the feature extraction unit 116 and the behavior recognition unit 118 to carry out the process relating to behavior recognition according to the configured setting relating to the behavior recognition in a way similar to the process (ii) (execution process) in the second information processing apparatus 200.

For example, the feature extraction unit 116 extracts a feature amount corresponding to a type of a feature amount to be used for the set behavior recognition from detection results obtained by the detection unit 104. The behavior recognition unit 118 recognizes predetermined behavior on the basis of the set algorithm and model data and the feature amount extracted by the feature extraction unit 116, for example.

The processing unit 114 causes the storage unit (not illustrated) or the connected recording medium such as the external recording medium to record the behavior-recognition-result information indicating a recognition result of the behavior recognized by the behavior recognition unit 118, for example.

In the processing unit 114, the recognition result of the behavior recognized by the behavior recognition unit 118 may be transmitted from the behavior recognition unit 118 to the behavior-recognition-mode setting unit 112, for example. The behavior-recognition-mode setting unit 112 to which the recognition result of the behavior has been transmitted sets (or resets) the behavior recognition mode further on the basis of the transmitted recognition result of behavior. The behavior-recognition-mode setting unit 112 sets (or resets) the behavior recognition mode by using the setting information, for example.

In addition, for example, the processing unit 114 causes the behavior-recognition-result information to be transmitted to the external apparatus such as another apparatus or a server constituting the information processing system according to the present embodiment, the behavior-recognition-result information indicating the recognition result of the behavior recognized by the behavior recognition unit 118. Examples of the another apparatus constituting the information processing system according to the present embodiment include the second information processing apparatus 200 (in the case where the information processing system according to the present embodiment is the information processing system 1000 according to the first embodiment) and another first information processing apparatus 300 (to be described later) (in the case where the information processing system according to the present embodiment is an information processing system 2000 according to the second embodiment.

In the case where the processing unit 114 causes the behavior-recognition-result information to be transmitted, the processing unit 114 causes the behavior-recognition-result information to be transmitted to the external apparatus every time the behavior recognition unit 118 recognizes behavior, for example. In the case where the processing unit 114 causes the behavior-recognition-result information to be transmitted, the processing unit 114 may cause the behavior-recognition-result information to be transmitted to the external apparatus when the behavior of the user recognized by the behavior recognition unit 118 has changed, for example.

The control unit 106 includes the status recognition unit 110, the behavior-recognition-mode setting unit 112, and the processing unit 114 for example, so as to lead the process relating to the information processing method according to the present embodiment.

The first information processing apparatus 100 carries out the process relating to the information processing method according to the present embodiment (for example, the process (1) (status recognition process) and the process (2) (behavior-recognition-mode setting process)) by the configuration illustrated in FIG. 13, for example.

Therefore, the first information processing apparatus 100 is capable of recognizing behavior of the user with a higher accuracy by the configuration illustrated in FIG. 13, for example.

In addition, by the configuration illustrated in FIG. 13, the first information processing apparatus 100 has effects such as the above described effect achieved by carrying out the process relating to the information processing method according to the present embodiment, for example.

The configuration of the first information processing apparatus according to the present embodiment is not limited to the configuration illustrated in FIG. 13, the first information processing apparatus constituting the information processing system 1000 according to the first embodiment.

For example, the first information processing apparatus according to the present embodiment may include one or more of the status recognition unit 110, the behavior-recognition-mode setting unit 112, and the processing unit 114 illustrated in FIG. 13 in addition to the control unit 106 (for example, they may be achieved by different processing circuits).

Alternatively, the first information processing apparatus according to the present embodiment does not have to include the processing unit 114 illustrated in FIG. 13. Even when the first information processing apparatus according to the present embodiment does not include the processing unit 114, the first information processing apparatus is capable of carrying out the process (1) (status recognition process) and the process (2) (behavior-recognition-mode setting process). Therefore, even when the first information processing apparatus according to the present embodiment does not include the processing unit 114, the first information processing apparatus is capable of recognizing behavior of a user with a higher accuracy.

In the following case, the first information processing apparatus according to the present embodiment does not have to include the detection unit 104, for example.

- The case where the first information processing apparatus according to the present embodiment carries out the process (1) (status recognition process) on the basis of information on a status of an apparatus indicating a detection result from the external sensor connected to the first information processing apparatus when the first information processing apparatus according to the present embodiment serves as the reference apparatus.
- The case where the first information processing apparatus 100 carries out the process (1) (status recognition process) on the basis of acquired information on a status of an apparatus when the first information processing apparatus 100 does not serve as the reference apparatus.

In the case where communication with the external apparatus is established via an external communication device having a function and configuration similar to the communication unit 102, the first information processing apparatus according to the present embodiment does not have to include the communication unit 102, for example.

The first information processing apparatus according to the present embodiment may have the configuration (for example, a setting unit to be described later) according to the second information processing apparatus according to the present embodiment (to be described later), for example.

[3-2] Example of Configuration of Second Information Processing Apparatus 200

Figure 15:
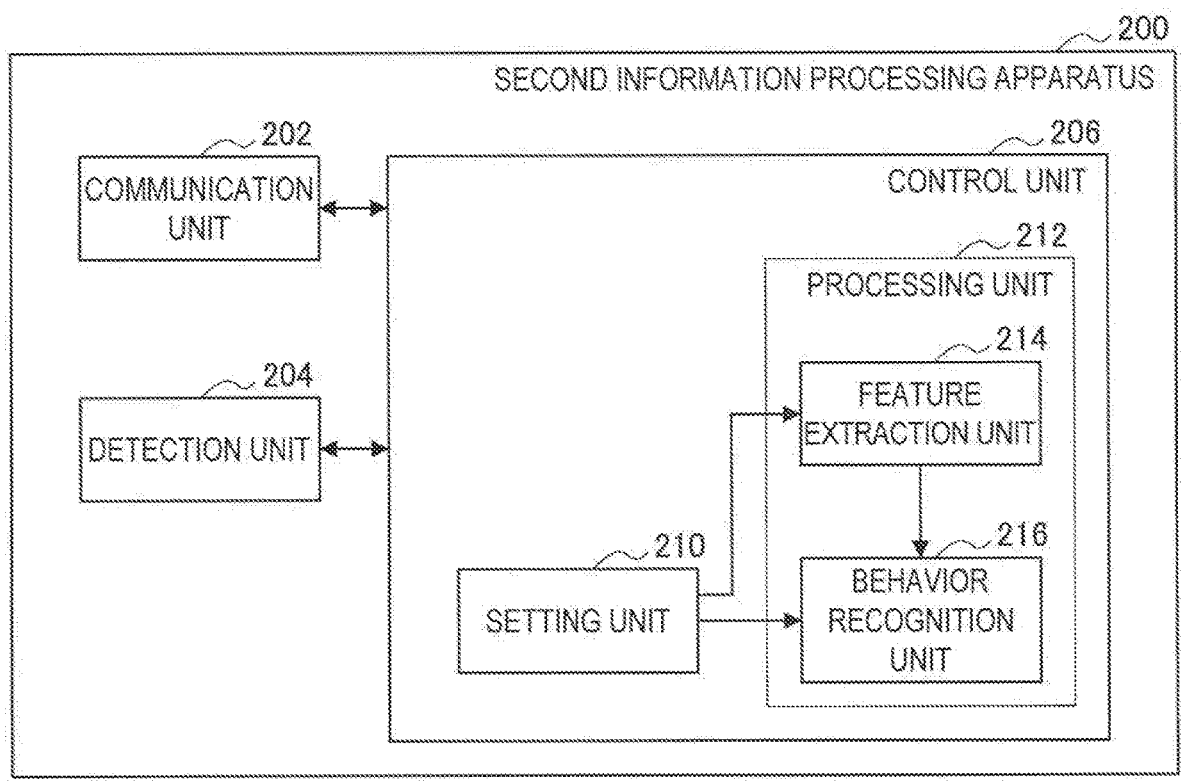
FIG. 15 is a block diagram illustrating an example of a configuration of a second information processing apparatus according to the present embodiment, the second information processing apparatus constituting an information processing system according to the first embodiment.

FIG. 15 is a block diagram illustrating an example of the configuration of the second information processing apparatus 200 according to the present embodiment, the second information processing apparatus constituting the information processing system 1000 according to the first embodiment. The second information processing apparatus 200 includes a communication unit 202, a detection unit 204, and a control unit 206, for example.

In addition, the second information processing apparatus 200 may include ROM (not illustrated), RAM (not illustrated), a storage unit (not illustrated), an operation unit (not illustrated) operated by a user, and a display unit (not illustrated) for displaying various screens on a display screen, for example. In the second information processing apparatus 200, the structural elements are connected via a bus serving as a data transmission channel, for example.

The ROM (not illustrated) stores control data used by the control unit 206 such as programs and operation parameters. The RAM (not illustrated) temporarily stores programs and the like executed by the control unit 206.

The storage unit (not illustrated) is a storage mechanism included in the second information processing apparatus 200. For example, the storage unit stores various kinds of data such as acquired information indicating a behavior recognition mode and an application. Examples of the storage unit (not illustrated) include a magnetic recording medium such as a hard disk, and nonvolatile memory such as flash memory, for example. The storage unit (not illustrated) may be detachably attached to the second information processing apparatus 200.

Examples of the operation unit (not illustrated) includes the above described operation input device. Examples of the display unit (not illustrated) includes the above described display device.

[Hardware Configuration Example of Second Information Processing Apparatus 200]

The second information processing apparatus 200 has a hardware configuration similar to the first information processing apparatus 100 illustrated in FIG. 14 (including modification). Of course, the hardware configuration of the second information processing apparatus 200 according to the present embodiment is not limited to the hardware configuration similar to the first information processing apparatus 100.

The communication unit 202 is a communication mechanism included in the second information processing apparatus 200, and communicates with the external apparatus such as the first information processing apparatus 100 or the external reference apparatus in a wired/wireless manner via a network (or directly). The communication performed by the communication unit 202 is controlled by the control unit 206, for example.

For example, the communication unit 102 may have a configuration corresponding to any standard that enables communication such as a communication antenna and an RF circuit or such as a LAN terminal and a transmission/reception circuit, or any configuration capable of communicating with the external apparatus via the network.

The detection unit 204 is a mechanism for detecting statuses of apparatuses included in the second information processing apparatus 200. A detection result output from the detection unit 204 is used in the process (ii) (execution process) in a processing unit 212 (to be described later), for example. Examples of the detection unit 204 include any sensors to be used for the process for behavior recognition of a user, such as an acceleration sensor or a GPS device. The detection unit 204 may be constituted of a sensor group including a plurality of sensors.

The control unit 206 is constituted of the MPU or the like and serves to control the entire second information processing apparatus 200, for example. In addition, the control unit 206 includes a setting unit 210 and the processing unit 212 for example, and serves to carry out the process (i) (setting process) and the process (ii) (execution process).

The setting unit 210 serves to lead the process (i) (setting process), and configures a setting relating to behavior recognition on the basis of information indicating a behavior recognition mode. Specifically, as the setting of the detection unit 204, the setting unit 210 configures a setting of whether a sensor constituting the detection unit 204 is used, or a setting of a parameter of the sensor. As the setting of a feature extraction unit 214 (to be described later), the setting unit 210 configures a setting of a type of a feature amount to be used for behavior recognition among detection results from the detection unit 204, for example. As the setting of a behavior recognition unit 216 (to be described later), the setting unit 210 configures a setting of an algorithm and model data to be used for the process for behavior recognition, for example.

The processing unit 212 serves to lead the above described process (ii) (execution process). For example, the processing unit 212 includes the feature extraction unit 214 and the behavior recognition unit 216 to carry out the process relating to behavior recognition according to the configured setting relating to the behavior recognition.

For example, the feature extraction unit 214 extracts a feature amount corresponding to a type of a feature amount to be used for the set behavior recognition from detection results obtained by the detection unit 204. The behavior recognition unit 216 recognizes predetermined behavior on the basis of the set algorithm and model data and the feature amount extracted by the feature extraction unit 214, for example. Here, the storage unit (not illustrated) or the connected recording medium such as the external recording medium records a recognition result of the behavior recognized by the behavior recognition unit 216, for example. The recognition result of the behavior recognized by the behavior recognition unit 216 may be transmitted to the external apparatus such as the server via the communication unit 202, for example.

The control unit 206 includes a setting unit 210 and the processing unit 212 for example, to carry out the process (i) (setting process) and the process (ii) (execution process).

The second information processing apparatus 200 carries out the process (i) (setting process) and the process (ii) (execution process) by the configuration illustrated in FIG. 15, for example.

By the configuration illustrated in FIG. 15 for example, the second information processing apparatus 200 carries out the process relating to behavior recognition according to the behavior recognition mode set by the first information processing apparatus 100 to recognize behavior of a user. Accordingly, since the second information processing apparatus 200 has the configuration illustrated in FIG. 15, it is possible to realize the master-slave type information processing system capable of recognizing behavior of a user with a higher accuracy.

Note that, the configuration of the second information processing apparatus according to the present embodiment is not limited to the configuration in FIG. 15.

For example, the second information processing apparatus according to the present embodiment may include one or both of the setting unit 210 and the processing unit 212 illustrated in FIG. 15 in addition to the control unit 206 (for example, they are achieved by different processing circuits).

In the case where communication with the external apparatus is established via an external communication device having a function and configuration similar to the communication unit 202, the second information processing apparatus according to the present embodiment does not have to include the communication unit 202, for example.

In the case where the second information processing apparatus according to the present embodiment is connected to an external sensor having a function and configuration similar to the detection unit 204, the second information processing apparatus according to the present embodiment does not have to include the detection unit 204, for example.

The second information processing apparatus according to the present embodiment may further include the status recognition unit 110 and the behavior-recognition-mode setting unit 112 illustrated in FIG. 13, for example. In the case where the second information processing apparatus according to the present embodiment further includes the status recognition unit 110 and the behavior-recognition-mode setting unit 112, the second information processing apparatus according to the present embodiment is further capable of functioning as the first information processing apparatus according to the present embodiment.

Information Processing System According to Second Embodiment

The information processing system according to the present embodiment is not limited to the master-slave type information processing system. Therefore, next, a peer-to-peer (P2P) type information processing system will be described as the information processing system according to the second embodiment according to the present embodiment. In the P2P type information processing system, each of apparatuses constituting the information processing system according to the present embodiment serves as the first information processing apparatus according to the present embodiment.

In the information processing system according to the second embodiment, each of the first information processing apparatuses constituting the information processing system according to the second embodiment shares one or more of a status of an apparatus that has recognized its own apparatus as the reference apparatus, behavior-recognition-result information corresponding to the own apparatus serving as the reference apparatus, and the behavior recognition mode set for the own apparatus, with the first information processing apparatuses. Thereby a behavior recognition mode is set for each of the first information processing apparatuses.

Figure 16:
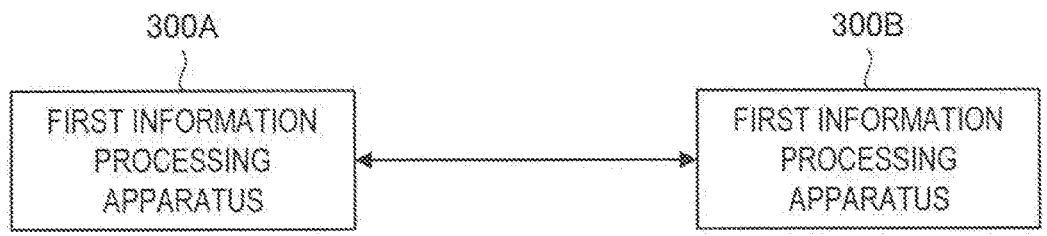
FIG. 16 is an explanatory diagram illustrating an example of an information processing system according to a second embodiment.

FIG. 16 is an explanatory diagram illustrating an example of the information processing system 2000 according to the second embodiment. The second information processing system 2000 includes a first information processing apparatus 300A, and a first information processing apparatus 300B, for example. Hereinafter, a set of the first information processing apparatuses 300A and 300B or one of the first information processing apparatuses 300A and 300B may be referred to as a "first information processing apparatus 300".

FIG. 16 illustrates the example in which the information processing system according to the second embodiment includes two first information processing apparatuses 300. However, the configuration of the information processing system according to the second embodiment is not limited thereto. For example, the information processing system according to the second embodiment may include there or more first information processing apparatuses 300.

[I] Process in First Information Processing Apparatus 300

The first information processing apparatus 300 carries out (I) status recognition process and (II) behavior-recognition-mode setting process as the process in the information processing method according to the present embodiment, so as to set a behavior recognition mode for its own apparatus serving as the setting target apparatus, for example.

(1) Status Recognition Process

The first information processing apparatus 300 recognizes a status of its own apparatus on the basis of information on a status of an apparatus corresponding to the own apparatus serving as the reference apparatus (first information processing apparatus 300). The first information processing apparatus 300 carries out a process similar to the process (1) (status recognition process) to recognize the status of the own apparatus.

The first information processing apparatus 300 causes the information indicating the recognized status of the own apparatus to be transmitted to another first information processing apparatus 300 (external apparatus) constituting the information processing system 2000. For example, the first information processing apparatus 300 causes a communication unit (to be described later) included in the first information processing apparatus 300 or the external communication device connected to the first information processing apparatus 300 to transmit the information indicating the status of the own apparatus to the another first information processing apparatus 300. Examples of the information indicating the status of the own apparatus according to the present embodiment include any type of data indicating a status of the own apparatus.

For example, the first information processing apparatus 300 causes the information indicating the status of the own apparatus to be transmitted with each recognition of a status of the own apparatus. In addition, the first information processing apparatus 300 may cause the information indicating the status of the own apparatus to be transmitted in the case where the recognized status of the own apparatus has changed, for example.

(II) Behavior-Recognition-Mode Setting Process

The first information processing apparatus 300 sets a behavior recognition mode for its own apparatus on the basis of the status of the own apparatus recognized in the process (I) (status recognition process), the behavior-recognition-result information corresponding to the own apparatus, and the acquired information on the external apparatus, for example.

Here, the information indicating the status of the external apparatus according to the present embodiment is data indicating the status of the own apparatus (another first information processing apparatus 300) recognized by the another first information processing apparatus 300.

The information on the external apparatus according to the present embodiment is data transmitted from another first information processing apparatus 300 (external apparatus) constituting the information processing system 2000. Examples of the information on the external apparatus according to the present embodiment include one or more of information indicating the status of the external apparatus, behavior-recognition-result information corresponding to the external apparatus, and information indicating a behavior recognition mode set in the external apparatus. Examples of the information indicating the status of the external apparatus according to the present embodiment include any type of data indicating a status of the external apparatus. The behavior-recognition-result information corresponding to the external apparatus according to the present embodiment is behavior-recognition-result information corresponding to the another first information processing apparatus 300.

The first information processing apparatus 300 specifies the behavior recognition mode set for its own apparatus by using setting information such as a table and database that define combinations of the "status of the own apparatus", the "behavior recognition result corresponding to the own apparatus", the "behavior recognition mode set for the own apparatus", and "one or more of the status of the external apparatus, the behavior recognition result corresponding to the external apparatus, and the behavior recognition mode corresponding to the external apparatus". Subsequently, the first information processing apparatus 300 sets the specified behavior recognition mode for the own apparatus.

The first information processing apparatus 300 causes information (data) indicating the set behavior recognition mode to be transmitted to the another first information processing apparatus 300 (external apparatus) constituting the information processing system 2000. For example, the first information processing apparatus 300 causes the information indicating the behavior recognition mode to be transmitted every time the behavior recognition mode is set. In addition, the first information processing apparatus 300 may cause the information indicating the behavior recognition mode to be transmitted in the case where the set behavior recognition mode has changed, for example.

The first information processing apparatus 300 causes the behavior-recognition-result information corresponding to its own apparatus to be transmitted to the another first information processing apparatus 300 (external apparatus). For example, the first information processing apparatus 300 causes the behavior-recognition-result information to be transmitted with each acquisition of the behavior-recognition-result information corresponding to the own apparatus. In addition, the first information processing apparatus 300 may cause the behavior-recognition-result information to be transmitted in the case where recognized behavior of a user indicated by the acquired behavior-recognition-result information has changed, for example.

For example, the first information processing apparatus 300 causes the communication unit (to be described later) included in the first information processing apparatus 300 or the external communication device connected to the first information processing apparatus 300 to transmit the information indicating the set behavior recognition mode, the behavior-recognition-result information corresponding to the own apparatus, and the like to the another first information processing apparatus 300.

In the information processing system 2000 according to the second embodiment, for example, each of the first information processing apparatuses 300 transmits, to another first information processing apparatus 300, information indicating a recognized status of its own apparatus, information indicating a set behavior recognition mode, and behavior-recognition-result information corresponding to the own apparatus. Therefore, in the information processing system 2000, the first information processing apparatuses share the status of the apparatus under a situation where the own apparatus is recognized as the reference apparatus, the behavior recognition mode set for the own apparatus, the behavior-recognition-result information corresponding to the own apparatus serving as the reference apparatus.

In the P2P type information processing system 2000, each of the first information processing apparatuses 300 carries out the process (I) (status recognition process) and the process (II) (behavior-recognition-mode setting process). Thereby each of the first information processing apparatus 300 sets the behavior recognition mode for its own apparatus (first information processing apparatus 300) serving as the setting target apparatus.

Accordingly, since the first information processing apparatus 300 carries out the process (I) (status recognition process) and the process (II) (behavior-recognition-mode setting process) as the processes in the information processing method according to the present embodiment, it is possible to realize the P2P type information processing system capable of recognizing behavior of a user with a higher accuracy.

Figure 17:
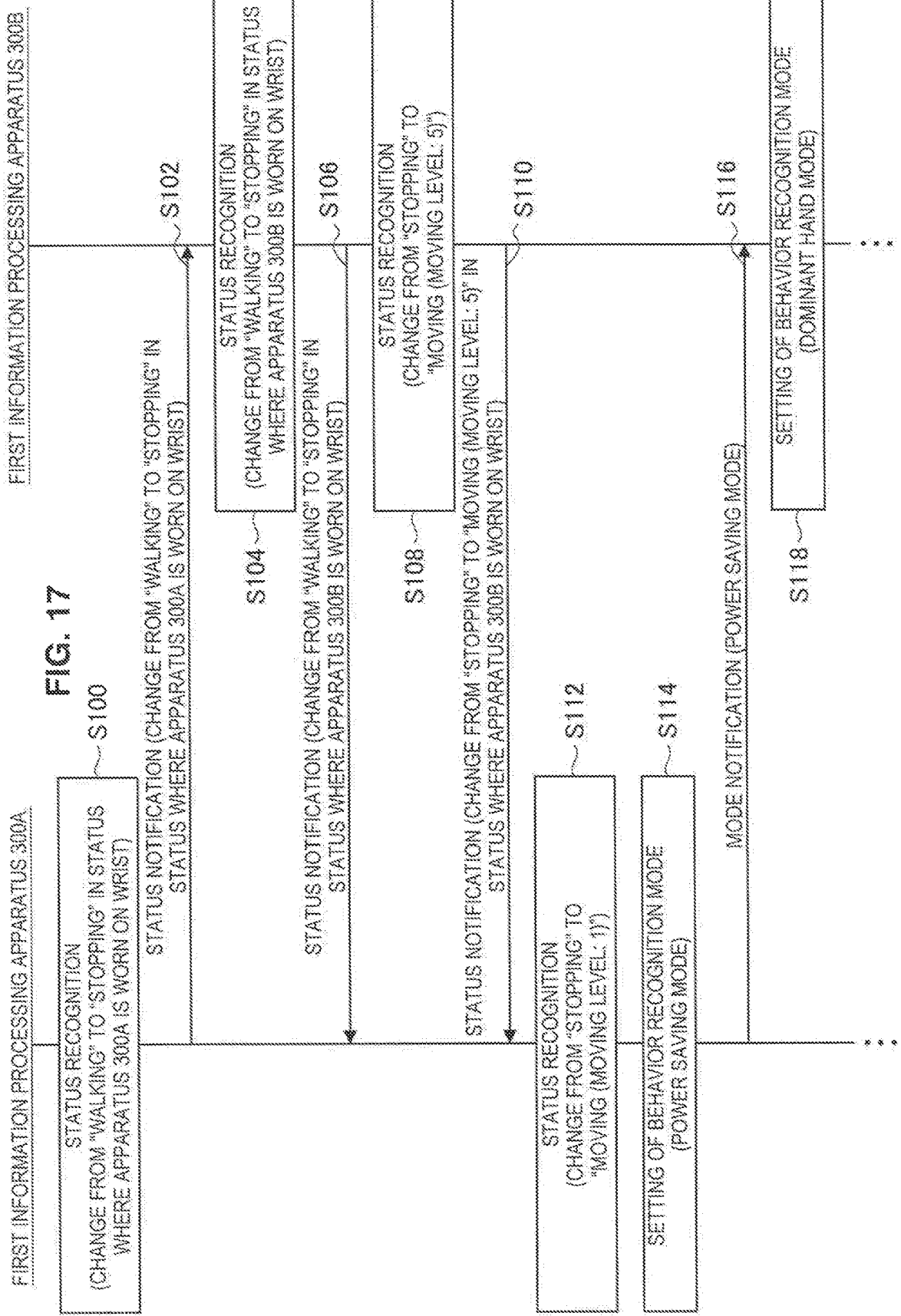
FIG. 17 is an explanatory diagram illustrating an example of a process in an information processing system according to the second embodiment.

Details of the process carried out in the information processing system 2000 will be described. FIG. 17 is an explanatory diagram illustrating an example of the process in the information processing system 2000 according to the second embodiment.

The first information processing apparatus 300A recognizes its status (S100). Step S100 is an example in which the first information processing apparatus 300A is recognized to be in a status where the apparatus 300A is worn on a wrist of a user by carrying out the process (I) (status recognition process). In addition, Step S100 is an example in which the first information processing apparatus 300A is recognized to be changed from "walking" to "stopping" according to behavior-recognition-result information.

Subsequently, the first information processing apparatus 300A transmits information indicating the recognized status of its own apparatus and the behavior-recognition-result information corresponding to the own apparatus to the first information processing apparatus 300B so as to notify the first information processing apparatus 300B of the status (S102).

The first information processing apparatus 300B recognizes its status (S104). Step S104 is an example in which the first information processing apparatus 300B is recognized to be in a status where the apparatus 300B is worn on a wrist of the user by carrying out the process (I) (status recognition process). In addition, Step S104 is an example in which the first information processing apparatus 300B is recognized to be changed from "walking" to "stopping" according to behavior-recognition-result information.

Subsequently, the first information processing apparatus 300B transmits information indicating the recognized status of its own apparatus and the behavior-recognition-result information corresponding to the own apparatus to the first information processing apparatus 300A so as to notify the first information processing apparatus 300A of the status (S106).

The first information processing apparatus 300B recognizes its status (S108). Step S108 is an example in which the first information processing apparatus 300B is recognized to be changed from "stopping" to "moving (moving level: 5)" according to behavior-recognition-result information. Here, for example, the first information processing apparatus 300B determines the moving level by carrying out a threshold process using a detection value from a sensor. In FIG. 17, a smaller value of the moving level represents smaller movement.

Subsequently, the first information processing apparatus 300B transmits information indicating the recognized status of its own apparatus and the behavior-recognition-result information corresponding to the own apparatus to the first information processing apparatus 300A so as to notify the first information processing apparatus 300A of the status (S110).

The first information processing apparatus 300A recognizes its status (S112). Step S112 is an example in which the first information processing apparatus 300A is recognized to be changed from "stopping" to "moving (moving level: 1)" according to behavior-recognition-result information. Here, for example, the first information processing apparatus 300A determines the moving level by carrying out a threshold process using a detection value from a sensor. Examples of the case where the moving level is determined to be 1 include a case where the movement is small and continuous.

The first information processing apparatus 300A carries out the process (II) (behavior-recognition-mode setting process) to set the behavior recognition mode of its own apparatus to a "power saving mode" (S114). For example, the first information processing apparatus 300A compares a moving level recognized by the first information processing apparatus 300A with a moving level in the first information processing apparatus 300B. In the example in FIG. 17, the first information processing apparatus 300A is set to be in the "power saving mode" since the moving level recognized by the first information processing apparatus 300A is lower. Subsequently, the first information processing apparatus 300A transmits information indicating the set behavior recognition mode to the first information processing apparatus 300B so as to notify the first information processing apparatus 300B of the behavior recognition mode (S116). Note that, in a way similar to Step S102, the first information processing apparatus 300A may transmit information indicating the recognized status of its own apparatus and the behavior-recognition-result information corresponding to the own apparatus to the first information processing apparatus 300B in Step S116.

The first information processing apparatus 300B carries out the process (II) (behavior-recognition-mode setting process) to set the behavior recognition mode of its own apparatus to a "dominant hand mode" (S118). For example, the first information processing apparatus 300B is set to be in the "dominant hand mode" since the behavior recognition mode set in the first information processing apparatus 300A is the "power saving mode", and the "motion (moving level: 5)" has been recognized in the first information processing apparatus 300B, and the first information processing apparatus 300B is worn on a wrist, for example. In addition, for example, in a way similar to Step S114, the first information processing apparatus 300B may be set to be in the "dominant hand mode" by comparing the moving level recognized in the first information processing apparatus 300A with the moving level in the first information processing apparatus 300B. In the example in FIG. 17, the first information processing apparatus 300B is set to be in the "dominant hand mode" since the moving level recognized in the first information processing apparatus 300B is higher, and the first information processing apparatus 300B is worn on the wrist.

Subsequently, in the information processing system 2000, each of the first information processing apparatus 300A and the first information processing apparatus 300B issues notification at a timing when the notification is necessary (for example, when the status has changed significantly).

In the information processing system 2000, a behavior recognition mode is set (or reset) in each of the first information processing apparatus 300A and the first information processing apparatus 300B by carrying out the process illustrated in FIG. 17, for example. Of course, the process in the information processing system 2000 is not limited to the example illustrated in FIG. 17.

[II] Configuration of First Information Processing Apparatus 300

Next, an example of the configuration of the first information processing apparatus 300 constituting the information processing system 2000 according to the second embodiment will be described.

Figure 18:
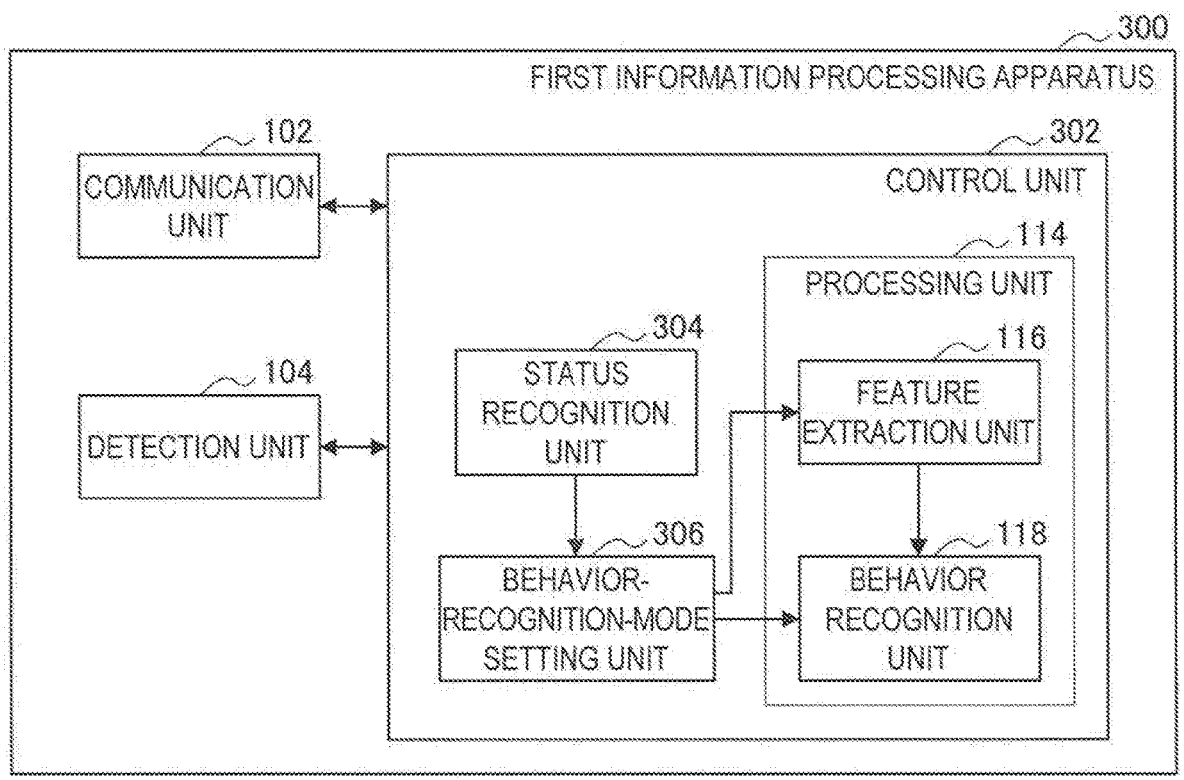
FIG. 18 is a block diagram illustrating an example of a configuration of a first information processing apparatus according to the present embodiment, the first information processing apparatus constituting an information processing system according to the second embodiment.

FIG. 18 is a block diagram illustrating an example of the configuration of the first information processing apparatus 300 according to the present embodiment, the first information processing apparatus constituting the information processing system 2000 according to the second embodiment.

The first information processing apparatus 300 has basically the same configuration as that of the first information processing apparatus 100, by comparing the first information processing apparatus 300 constituting the information processing system 2000 illustrated in FIG. 18 with the first information processing apparatus 100 constituting the information processing system 1000 illustrated in FIG. 13. Accordingly, hereinafter, a control unit 302 for leading the process in the information processing method according to the present embodiment is mainly described among the structural elements in the first information processing apparatus 300 illustrated in FIG. 18. Descriptions of the other structural elements are omitted.

The control unit 302 is constituted of the MPU or the like and serves to control the entire first information processing apparatus 300. In addition, the control unit 302 includes the status recognition unit 304, the behavior-recognition-mode setting unit 306, and the processing unit 114 for example, and serves to lead the process relating to the information processing method according to the present embodiment.

The control unit 302 may further include a communication control unit (not illustrated) for controlling communication in the communication unit 102, for example. The communication control unit (not illustrated) carries out a process for controlling exchange of various kinds of information and for understanding a status of another first information processing apparatus 300 constituting the information processing system 2000. The function of the communication control unit (not illustrated) may be carried out by another structural element such as the communication unit 102.

The status recognition unit 304 serves to lead the process (I) (status recognition process) to recognize a status of the reference apparatus on the basis of information on a status of an apparatus. The status recognition unit 304 carries out a process similar to the status recognition unit 110 illustrated in FIG. 13 to recognize a status of a reference apparatus, for example.

The behavior-recognition-mode setting unit 306 serves to lead the above described process (II) (behavior-recognition-mode setting process). The behavior-recognition-mode setting unit 306 sets a behavior recognition mode for its own apparatus on the basis of a status of the own apparatus recognized by the status recognition unit 304, the behavior-recognition-result information corresponding to the own apparatus, and information on the external apparatus acquired through communication in the communication unit 102. The behavior-recognition-mode setting unit 306 sets the behavior recognition mode for its own apparatus by configuring one or more of a setting of the detection unit 104, a setting of the feature extraction unit 116, and a setting of the behavior recognition unit 118, in a way similar to the process carried out in the case where the behavior-recognition-mode setting unit 112 in FIG. 13 sets the behavior recognition mode for its own apparatus, for example.

For example, like the processing unit 114 illustrated in FIG. 13, the processing unit 114 includes the feature extraction unit 116 and the behavior recognition unit 118 to carry out the process relating to behavior recognition according to the configured setting relating to the behavior recognition in a way similar to the processing unit 114 illustrated in FIG. 13.

The processing unit 114 causes the behavior-recognition-result information to be transmitted to the another first information processing apparatus 300 (external apparatus) constituting the information processing system 2000, the behavior-recognition-result information indicating the recognition result of the behavior recognized by the behavior recognition unit 118. Here, for example, the processing unit 114 causes the behavior-recognition-result information to be transmitted to the another first information processing apparatus 300 every time the behavior recognition unit 118 recognizes behavior. In addition, for example, the processing unit 114 causes the behavior-recognition-result information to be transmitted to the another first information processing apparatus 300 in the case where the behavior of the user recognized by the behavior recognition unit 118 has changed.

The control unit 302 includes the status recognition unit 304, the behavior-recognition-mode setting unit 306, and the processing unit 114 to lead the process relating to the information processing method according to the present embodiment, for example.

The first information processing apparatus 300 carries out the process relating to the information processing method according to the present embodiment (for example, the process (I) (status recognition process) and the process (II) (behavior-recognition-mode setting process)) by the configuration illustrated in FIG. 18, for example.

Therefore, the first information processing apparatus 300 is capable of recognizing behavior of the user with a higher accuracy by the configuration illustrated in FIG. 18, for example.

In addition, by the configuration illustrated in FIG. 18, the first information processing apparatus 300 achieves effects such as the above described effect achieved by carrying out the process relating to the information processing method according to the present embodiment, for example.

The configuration of the first information processing apparatus according to the present embodiment is not limited to the configuration illustrated in FIG. 18, the first information processing apparatus constituting the information processing system 2000 according to the second embodiment.

For example, the first information processing apparatus according to the present embodiment may include one or more of the status recognition unit 304, the behavior-recognition-mode setting unit 306, and the processing unit 114 illustrated in FIG. 18 in addition to the control unit 302 (for example, they are achieved by different processing circuits).

The first information processing apparatus according to the present embodiment does not have to include the processing unit 114 illustrated in FIG. 18 in the case where there is an external apparatus having a function similar to the processing unit 114 and capable of recognizing behavior of a user corresponding to the first information processing apparatus according to the present embodiment, for example. Even when the first information processing apparatus according to the present embodiment does not include the processing unit 114, the first information processing apparatus is capable of carrying out the process (I) (status recognition process) and the process (II) (behavior-recognition-mode setting process). Therefore, even when the first information processing apparatus according to the present embodiment does not include the processing unit 114, the first information processing apparatus is capable of recognizing behavior of a user with a higher accuracy.

For example, the first information processing apparatus according to the present embodiment does not have to include the detection unit 104 in the case where the first information processing apparatus according to the present embodiment carries out the process (I) (status recognition process) on the basis of information on a status of an apparatus indicating a detection result from the external sensor connected to the first information processing apparatus.

In the case where communication with the external apparatus is established via an external communication device having a function and configuration similar to the communication unit 102, the first information processing apparatus according to the present embodiment does not have to include the communication unit 102, for example.

The first information processing apparatus according to the present embodiment may further include the setting unit 210 illustrated in FIG. 15, for example. In the case where the first information processing apparatus according to the present embodiment further includes the setting unit 210, the first information processing apparatus according to the present embodiment is further capable of functioning as the second information processing apparatus according to the present embodiment.

The first information processing apparatus has been described as the structural element of the information processing system according to the present embodiment. However, the present embodiment is not limited thereto. The present embodiment is applied to various kinds of portable equipment such as a communication apparatus like a mobile phone or a smartphone, a tablet apparatus, a video/music reproduction apparatus (or video/music recording and reproduction apparatus), a game console, and a computer such as a laptop personal computer (PC). The present embodiment may also be applied to a wearable apparatus, for example. The present embodiment may also be applied to the various equipment difficult to carry such as a server or a computer like a desktop PC. In addition, the present embodiment may also be applied to a processing integrated circuit (IC) which can be installed in the above described equipment.

In the case where the first information processing apparatus is applied to the equipment difficult to carry such as a server or a computer like a desktop PC, the master-slave type information processing system according to the first embodiment may be achieved as a cloud-computing type information processing system, for example.

The second information processing apparatus has been described as the structural element of the information processing system according to the present embodiment. However, the present embodiment is not limited thereto. The present embodiment is applied to various kinds of portable equipment such as a communication apparatus like a mobile phone or a smartphone, a tablet apparatus, a video/music reproduction apparatus (or video/music recording and reproduction apparatus), a game console, and a computer such as a laptop PC. The present embodiment may also be applied to a wearable apparatus, for example. In addition, the present embodiment may also be applied to a processing IC which can be installed in the above described equipment.

Program According to Present Embodiment

[i] Program Relating to First Information Processing Apparatus

A program for causing a computer to function as the first information processing apparatus according to the present embodiment (for example, program capable of executing the process relating to the information processing method according to the present embodiment, such as the process (1) (status recognition process), and the process (2) (behavior-recognition-mode setting process)", or the process (I) (status recognition process) and the process (II) (behavior-recognition-mode setting process)") is executed by a processor or the like in the computer. Thereby, it is possible to recognize behavior of a user with a higher accuracy.

In addition, the processor or the like in the computer executes the program for causing the computer to function as the first information processing apparatus according to the present embodiment. Thereby, it is possible to achieve the master-slave type information processing system or the PSP type information processing system capable of recognizing behavior of a user with a higher accuracy. In addition, the processor or the like in the computer executes the program for causing the computer to function as the first information processing apparatus according to the present embodiment. Thereby, it is possible to achieve the effect to be achieved by the process in the information processing method according to the present embodiment.

[ii] Program Relating to Second Information Processing Apparatus

A program for causing a computer to function as the second information processing apparatus according to the present embodiment (for example, program capable of executing the process (i) (setting process), and the process (ii) (execution process)) is executed by a processor or the like in the computer. Thereby, it is possible to recognize behavior of a user by carrying out the process relating to behavior recognition corresponding to the behavior recognition mode set by the first information processing apparatus constituting the information processing system according to the first embodiment. Accordingly, the processor or the like in the computer executes the program for causing the computer to function as the second information processing apparatus according to the present embodiment. Thereby, it is possible to achieve the master-slave type information processing system capable of recognizing behavior of a user with a higher accuracy.

The preferred embodiments of the present disclosure have been described above with reference to the accompanying drawings, whilst the present invention is not limited to the above examples, of course. A person skilled in the art may find various alternations and modifications within the scope of the appended claims, and it should be understood that they will naturally come under the technical scope of the present disclosure.

For example, the program (computer program) for causing the computer to function as the first information processing apparatus according to the present embodiment or the second information processing apparatus according to the present embodiment has been provided above. However, the present embodiment can also provide recording media each on which each of the above described programs is stored, or a recording medium on which the both programs are stored together.

The above configuration shows an example of the present embodiment and naturally comes under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1) An information processing apparatus including:
a status recognition unit configured to recognize a status of a reference apparatus on the basis of information on a status of an apparatus corresponding to the reference apparatus, the reference apparatus serving as a reference when a behavior recognition mode for deciding a status of behavior is set; and
a behavior-recognition-mode setting unit configured to set the behavior recognition mode for a setting target apparatus for which the behavior recognition mode is to be set on the basis of the recognized status of the reference apparatus.

(2) The information processing apparatus according to (1),
wherein the behavior-recognition-mode setting unit sets the behavior recognition mode further on the basis of behavior-recognition-result information indicating a recognition result of behavior of a user corresponding to the reference apparatus.

(3) The information processing apparatus according to (2),
wherein the setting target apparatus includes the reference apparatus, and
wherein, in a case where the behavior recognition mode has been set for the reference apparatus, the behavior-recognition-mode setting unit sets the behavior recognition mode for the setting target apparatus on the basis of the behavior-recognition-result information indicating a recognition result of behavior of a user recognized on the basis of a setting relating to behavior recognition indicated by the behavior recognition mode set for the reference apparatus.

(4) The information processing apparatus according to (2) or (3),
wherein the behavior-recognition-mode setting unit sets the behavior recognition mode with each change in the recognized status of the reference apparatus or the recognition result of behavior of the user indicated by the behavior-recognition-result information.

(5) The information processing apparatus according to any one of (2) to (4),
wherein the behavior-recognition-mode setting unit
specifies the behavior recognition mode corresponding to the recognized status of the reference apparatus and the behavior-recognition-result information by using setting information in which a status of an apparatus, behavior of a user, and the behavior recognition mode are associated with each other, and
sets the specified behavior recognition mode for the setting target apparatus.

(6) The information processing apparatus according to (5),
wherein the association between the status of the apparatus, the behavior of the user, and the behavior recognition mode in the setting information is updated on the basis of a user operation for directly updating the association or a user operation for indirectly updating the association.

(7) The information processing apparatus according to any one of (1) to (6),
wherein the setting target apparatus includes an apparatus other than the reference apparatus, and
wherein, in a case where there are a plurality of apparatuses other than the reference apparatus, the behavior-recognition-mode setting unit sets the behavior recognition mode for each of the apparatuses other than the reference apparatus.

(8) The information processing apparatus according to any one of (1) to (7),
wherein the setting target apparatus includes an apparatus other than the reference apparatus, and
wherein the behavior-recognition-mode setting unit sets the behavior recognition mode for the setting target apparatus, further on the basis of a relative distance between the reference apparatus and the apparatus other than the reference apparatus.

(9) The information processing apparatus according to (2),
wherein the status recognition unit recognizes a status of the own apparatus as a status of the reference apparatus, on the basis of information on a status of the apparatus corresponding to the own apparatus, and
wherein the behavior-recognition-mode setting unit
sets the setting target apparatus for which the behavior recognition mode is set, as the own apparatus, and
sets the behavior recognition mode for the own apparatus on the basis of the recognized status of the own apparatus, the behavior-recognition-result information corresponding to the own apparatus, and acquired information on an external apparatus.

(10) The information processing apparatus according to (9), further including
a processing unit configured to carry out a process relating to behavior recognition according to a setting relating to the behavior recognition indicated by the set behavior recognition mode,
wherein the status recognition unit causes information indicating the recognized status of the own apparatus to be transmitted to the external apparatus,
wherein the behavior-recognition-mode setting unit causes information indicating the set behavior recognition mode to be transmitted to the external apparatus, and
wherein the processing unit causes the behavior-recognition-result information corresponding to the recognized behavior of the user to be transmitted to the external apparatus.

(11) The information processing apparatus according to (10),
wherein, in a case where the recognized status of the own apparatus has changed, the status recognition unit causes the information indicating the status of the own apparatus to be transmitted to the external apparatus,
wherein, in a case where the set behavior recognition mode has changed, the behavior-recognition-mode setting unit causes the information indicating the behavior recognition mode to be transmitted to the external apparatus, and
wherein, in a case where the recognized behavior of the user has changed, the processing unit causes the behavior-recognition-result information to be transmitted to the external apparatus.

(12) An information processing apparatus including:
a setting unit configured to configure a setting relating to behavior recognition on the basis of information indicating a behavior recognition mode for deciding a status of acquired behavior; and
a processing unit configured to carry out a process relating to the behavior recognition according to the configured setting relating to the behavior recognition.

(13) The information processing apparatus according to (12),
wherein the processing unit carries out the process relating to the behavior recognition on the basis of a relative distance from a reference apparatus serving as a reference of the behavior recognition mode to be set.

(14) The information processing apparatus according to (12),
wherein the processing unit carries out the process relating to the behavior recognition on the basis of a position of the own apparatus.

(15) An information processing method carried out by an information processing apparatus, the method including:

a step of recognizing a status of a reference apparatus on the basis of information on a status of an apparatus corresponding to the reference apparatus, the reference apparatus serving as a reference of a behavior recognition mode for deciding a status of behavior; and
a step of setting the behavior recognition mode for a setting target apparatus for which the behavior recognition mode is to be set on the basis of the recognized status of the reference apparatus.

(16) A program causing a computer to execute:
a step of recognizing a status of a reference apparatus on the basis of information on a status of an apparatus corresponding to the reference apparatus, the reference apparatus serving as a reference of a behavior recognition mode for deciding a status of behavior; and
a step of setting the behavior recognition mode for a setting target apparatus for which the behavior recognition mode is to be set on the basis of the recognized status of the reference apparatus.

(17) An information processing system including:
a first information processing apparatus configured to set a behavior recognition mode for a setting target apparatus for which the behavior recognition mode for deciding a status of behavior is to be set; and
one or more of second information processing apparatuses each of which is the setting target apparatus and each of which is configured to carry out a process relating to behavior recognition on the basis of the set behavior recognition mode,
wherein the first information processing apparatus includes
a status recognition unit configured to recognize a status of a reference apparatus on the basis of information on a status of an apparatus corresponding to the reference apparatus, the reference apparatus serving as a reference of the behavior recognition mode, and
a behavior-recognition-mode setting unit configured to set the behavior recognition mode for each of the second information processing apparatuses on the basis of the recognized status of the reference apparatus.

REFERENCE SIGNS LIST 100, 300, 300a, 300b first information processing apparatus
102, 202 communication unit
104, 204 detection unit
106, 206, 302 control unit
110, 304 status recognition unit
112, 306 behavior-recognition-mode setting unit
114, 212 processing unit
116, 214 feature extraction unit
118, 216 behavior recognition unit
200, 200a, 200b second information processing apparatus
210 setting unit

The invention claimed is:
1. An information processing apparatus, comprising:
a processor configured to:
acquire, from at least one sensor, first information associated with a status of a reference apparatus;
recognize the status of the reference apparatus based on the first information;
determine a relative distance between the reference apparatus and each of a plurality of setting target apparatuses; and
control the plurality of setting target apparatuses to set a first behavior recognition mode of a first setting target apparatus of the plurality of setting target apparatuses and to set a second behavior recognition mode of a second setting target apparatus of the plurality of setting target apparatuses, wherein the first behavior recognition mode and the second behavior recognition mode correspond to recognition of different user behaviors, and the plurality of setting target apparatuses is controlled based on:
the recognized status of the reference apparatus,
the relative distance between the reference apparatus and each of the first setting target apparatus and the second setting target apparatus, and
transmission of information indicating a respective behavior recognition mode from the reference apparatus to one of the plurality of setting target apparatuses in case the relative distance to the one of the plurality of setting target apparatuses is longer than a threshold.

2. The information processing apparatus according to claim 1, wherein
the processor is further configured to set the first behavior recognition mode based on first behavior-recognition-result information, and
the first behavior-recognition-result information indicates a recognition result of a user behavior corresponding to the reference apparatus.

3. The information processing apparatus according to claim 2, wherein
the plurality of setting target apparatuses includes the reference apparatus,
the processor is further configured to control the plurality of setting target apparatuses to set the first behavior recognition mode based on a third behavior recognition mode of the reference apparatus and the first behavior-recognition-result information indicating the recognition result of the user behavior,
the user behavior is recognized based on a setting associated with behavior recognition, and
the setting is indicated by the third behavior recognition mode.

4. The information processing apparatus according to claim 2, wherein the processor is further configured to set the first behavior recognition mode based on at least one of a change in the recognized status of the reference apparatus, or the first behavior-recognition-result information.

5. The information processing apparatus according to claim 2, wherein the processor is further configured to:
specify the first behavior recognition mode, corresponding to each of the recognized status of the reference apparatus and the first behavior-recognition-result information, based on setting information that corresponds to an association between a specific status of a specific apparatus, the user behavior, and the first behavior recognition mode; and
control the first setting target apparatus to set the specified first behavior recognition mode of the first setting target apparatus.

6. The information processing apparatus according to claim 5, wherein
the association between the specific status of the specific apparatus, the user behavior, and the first behavior recognition mode in the setting information is updated based on a user operation, and
the user operation corresponds to one of a direct update of the association or an indirect update of the association.

7. The information processing apparatus according to claim 1, wherein the plurality of setting target apparatuses includes a plurality of apparatuses different from the reference apparatus, and
the processor is further configured to control each of the plurality of apparatuses to set a behavior recognition mode for each of the plurality of apparatuses.

8. The information processing apparatus according to claim 2, wherein the processor is further configured to:
recognize a status of the information processing apparatus as the status of the reference apparatus based on second information, wherein the second information is associated with the status of the information processing apparatus;
set the information processing apparatus as the first setting target apparatus; and
set a third behavior recognition mode for the information processing apparatus based on each of the recognized status of the information processing apparatus, second behavior-recognition-result information corresponding to the information processing apparatus, and third information that is acquired from an external apparatus.

9. The information processing apparatus according to claim 8, wherein the processor is further configured to:
execute a behavior recognition process based on a setting indicated by the set first behavior recognition mode;
transmit, to the external apparatus, fourth information indicating the recognized status of the information processing apparatus;
transmit, to the external apparatus, fifth information indicating the set first behavior recognition mode; and
transmit, to the external apparatus, the second behavior-recognition-result information.

10. The information processing apparatus according to claim 9, wherein the processor is further configured to:
transmit, to the external apparatus, the fourth information based on a change in the recognized status of the information processing apparatus;
transmit, to the external apparatus, the fifth information based on a change in the first behavior recognition mode; and
transmit the second behavior-recognition-result information to the external apparatus based on a change in the recognition result of the user behavior corresponding to the information processing apparatus.

11. An information processing apparatus, comprising:
a communication circuit configured to receive information associated with a first behavior recognition mode from an external apparatus, wherein the first behavior recognition mode is different from a second behavior recognition mode set for an external setting target apparatus, and the first behavior recognition mode and the second behavior recognition mode correspond to recognition of different user behaviors; and
a processor configured to:
control a setting for behavior recognition based on:
the received information that is associated with the first behavior recognition mode, and
a relative distance between a reference apparatus and the information processing apparatus that exceeds a threshold, wherein the reference apparatus is a reference for the first behavior recognition mode; and
execute a process for the behavior recognition based on the setting.

12. The information processing apparatus according to claim 11, wherein the processor is further configured to execute the process for the behavior recognition based on the relative distance from the reference apparatus.

13. The information processing apparatus according to claim 11, wherein the processor is further configured to execute the process for the behavior recognition based on a position of the information processing apparatus.

14. An information processing method, comprising:
in an information processing apparatus:
acquiring, from a sensor device, information associated with a status of a reference apparatus;
recognizing the status of the reference apparatus based on the information;
determining a relative distance between the reference apparatus and each of a plurality of setting target apparatuses; and
controlling the plurality of setting target apparatuses to set a first behavior recognition mode of a first setting target apparatus of the plurality of setting target apparatuses and to set a second behavior recognition mode of a second setting target apparatus of the plurality of setting target apparatuses, wherein the first behavior recognition mode and the second behavior recognition mode correspond to recognition of different user behaviors, and the plurality of setting target apparatuses is controlled based on:
the recognized status of the reference apparatus, and
the relative distance between the reference apparatus and each of the first setting target apparatus and the second setting target apparatus, and
transmission of information indicating a respective behavior recognition mode from the reference apparatus to one of the plurality of setting target apparatuses in case the relative distance to the one of the plurality of setting target apparatuses that is longer than a threshold.

15. A non-transitory computer-readable medium having stored thereon, computer-executable instructions, which when executed by a processor of an information processing apparatus, cause the processor to execute operations, the operations comprising:
acquiring, from a sensor device, information associated with a status of a reference apparatus;
recognizing the status of the reference apparatus based on the information;
determining a relative distance between the reference apparatus and each of a plurality of setting target apparatuses; and
controlling the plurality of setting target apparatuses to set a first behavior recognition mode of a first setting target apparatus of the plurality of setting target apparatuses and to set a second behavior recognition mode of a second setting target apparatus of the plurality of setting target apparatuses, wherein the first behavior recognition mode and the second behavior recognition mode correspond to recognition of different user behaviors, and the plurality of setting target apparatuses is controlled based on:
the recognized status of the reference apparatus,
the relative distance between the reference apparatus and each of the first setting target apparatus and the second setting target apparatus, and
transmission of information indicating a respective behavior recognition mode from the reference apparatus to one of the plurality of the setting target apparatuses in case the relative distance to the one of the plurality of setting target apparatuses is longer than a threshold.

16. An information processing system, comprising:
a first information processing apparatus; and
a plurality of setting target apparatuses,
wherein
the first information processing apparatus includes a processor configured to:
acquire, from a sensor device, information associated with a status of a reference apparatus;
recognize the status of the reference apparatus based on the information;
determine a relative distance between the reference apparatus and each of the plurality of setting target apparatuses; and
control the plurality of setting target apparatuses to set a first behavior recognition mode of a first setting target apparatus of the plurality of setting target apparatuses and to set a second behavior recognition mode of a second setting target apparatus of the plurality of setting target apparatuses, wherein the first behavior recognition mode and the second behavior recognition mode correspond to recognition of different user behaviors, and the plurality of setting target apparatuses is controlled based on:
the recognized status of the reference apparatus,
the relative distance between the reference apparatus and each of the plurality of setting target apparatuses, and
transmission of information indicating a respective behavior recognition mode from the reference apparatus to one of the plurality of setting target apparatuses in case the relative distance to the one of the plurality of setting target apparatuses is longer than a threshold, and
each of the plurality of setting target apparatuses is configured to execute a behavior recognition process based on the respective behavior recognition mode.

* * * * *